(12) United States Patent
Sanders et al.

(10) Patent No.: US 11,147,958 B2
(45) Date of Patent: Oct. 19, 2021

(54) SYSTEM FOR CLOSED TRANSFER OF FLUIDS HAVING CONNECTOR

(71) Applicant: Becton Dickinson and Company Limited, Dun Laoghaire (IE)

(72) Inventors: Laurie Sanders, Glen Ridge, NJ (US); Matthew Zachek, Riverdale, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 25 days.

(21) Appl. No.: 15/478,500

(22) Filed: Apr. 4, 2017

(65) Prior Publication Data

US 2017/0203091 A1 Jul. 20, 2017

Related U.S. Application Data

(63) Continuation of application No. 14/532,188, filed on Nov. 4, 2014, now Pat. No. 9,642,775.

(60) Provisional application No. 61/900,623, filed on Nov. 6, 2013.

(51) Int. Cl.
  *A61M 39/10* (2006.01)
  *A61M 5/145* (2006.01)
  *A61J 1/20* (2006.01)

(52) U.S. Cl.
  CPC ........ *A61M 39/1011* (2013.01); *A61J 1/2006* (2015.05); *A61J 1/2072* (2015.05); *A61J 1/2096* (2013.01); *A61M 5/1452* (2013.01); *A61M 39/105* (2013.01); *A61J 1/201* (2015.05); *A61J 1/2051* (2015.05); *A61J 1/2075* (2015.05); *A61M 2039/1077* (2013.01)

(58) Field of Classification Search
  CPC ........ A61J 1/201; A61J 1/2051; A61J 1/2072; A61J 1/2075; A61J 1/2096; A61M 2039/1077; A61M 39/1011; A61M 39/105
  See application file for complete search history.

(56) References Cited

U.S. PATENT DOCUMENTS

| | | | |
|---|---|---|---|
| 4,436,125 | A | 3/1984 | Blenkush |
| 4,564,054 | A | 1/1986 | Gustavsson |
| 4,673,404 | A | 6/1987 | Gustavsson |
| 4,932,937 | A | 6/1990 | Gustavsson et al. |

(Continued)

FOREIGN PATENT DOCUMENTS

| | | | |
|---|---|---|---|
| EP | 2298407 A1 | 3/2011 | |
| EP | 2462971 A1 | 6/2012 | |

(Continued)

*Primary Examiner* — Quynh-Nhu H. Vu
(74) *Attorney, Agent, or Firm* — The Webb Law Firm

(57) ABSTRACT

A system includes a syringe adapter having a first end and a second end with the first end of the syringe adapter configured to be connected to a first container and the second end of the syringe adapter including a lock member having an open position and a closed position. The system also includes a vial adapter having a first end and a second end with the second end of the vial adapter configured to be connected to a second container and the first end of the vial adapter having a locking surface. The lock member includes at least one projection that extends radially outward. The syringe adapter has at least one corresponding projection configured to engage the at least one projection of the lock member to retain the lock member to the syringe adapter.

12 Claims, 20 Drawing Sheets

(56) References Cited

U.S. PATENT DOCUMENTS

| | | | |
|---|---|---|---|
| 5,052,725 A * | 10/1991 | Meyer | F16L 37/0841 285/308 |
| 5,104,158 A * | 4/1992 | Meyer | F16L 37/0841 285/308 |
| 5,122,129 A | 6/1992 | Olson et al. | |
| 5,280,876 A | 1/1994 | Atkins | |
| 5,290,254 A | 3/1994 | Vaillancourt | |
| 5,322,518 A | 6/1994 | Schneider et al. | |
| 5,334,188 A | 8/1994 | Inoue et al. | |
| 5,360,011 A | 11/1994 | McCallister | |
| 5,395,348 A | 3/1995 | Ryan | |
| 5,437,650 A | 8/1995 | Larkin et al. | |
| 5,464,123 A | 11/1995 | Scarrow | |
| 5,472,430 A | 12/1995 | Vaillancourt et al. | |
| 5,478,328 A | 12/1995 | Silverman et al. | |
| 5,487,728 A | 1/1996 | Vaillancourt | |
| 5,507,733 A | 4/1996 | Larkin et al. | |
| 5,509,911 A | 4/1996 | Cottone, Sr. et al. | |
| 5,545,152 A | 8/1996 | Funderburk et al. | |
| 5,607,392 A | 3/1997 | Kanner | |
| 5,609,584 A | 3/1997 | Gettig et al. | |
| 5,611,792 A | 3/1997 | Gustafsson | |
| 5,647,845 A | 7/1997 | Haber et al. | |
| 5,685,866 A | 11/1997 | Lopez | |
| 5,807,347 A | 9/1998 | Bonaldo | |
| 5,845,943 A * | 12/1998 | Ramacier, Jr. | F16L 37/0841 285/12 |
| 5,897,526 A | 4/1999 | Vaillancourt | |
| 6,063,068 A | 5/2000 | Fowles et al. | |
| 6,089,541 A | 7/2000 | Weinheimer et al. | |
| 6,113,583 A | 9/2000 | Fowles et al. | |
| 6,132,404 A | 10/2000 | Lopez | |
| 6,139,534 A | 10/2000 | Niedospial, Jr. et al. | |
| 6,183,465 B1 * | 2/2001 | Meier | A61M 5/162 604/533 |
| 6,221,041 B1 | 4/2001 | Russo | |
| 6,221,056 B1 | 4/2001 | Silverman | |
| 6,343,629 B1 | 2/2002 | Wessman et al. | |
| 6,358,236 B1 | 3/2002 | DeFoggi et al. | |
| 6,409,708 B1 | 6/2002 | Wessman | |
| 6,474,375 B2 | 11/2002 | Spero et al. | |
| 6,478,788 B1 | 11/2002 | Aneas | |
| 6,544,246 B1 | 4/2003 | Niedospial, Jr. | |
| 6,551,299 B2 | 4/2003 | Miyoshi et al. | |
| 6,585,695 B1 | 7/2003 | Adair et al. | |
| 6,599,273 B1 | 7/2003 | Lopez | |
| 6,610,040 B1 | 8/2003 | Fowles et al. | |
| 6,629,958 B1 | 10/2003 | Spinello | |
| 6,656,433 B2 | 12/2003 | Sasso | |
| 6,715,520 B2 | 4/2004 | Andreasson et al. | |
| 6,814,726 B1 | 11/2004 | Lauer | |
| 6,852,103 B2 | 2/2005 | Fowles et al. | |
| 6,875,203 B1 | 4/2005 | Fowles et al. | |
| 6,875,205 B2 | 4/2005 | Leinsing | |
| 6,911,025 B2 | 6/2005 | Miyahara | |
| 6,997,917 B2 | 2/2006 | Niedospial, Jr. et al. | |
| 7,040,598 B2 | 5/2006 | Raybuck | |
| 7,083,605 B2 | 8/2006 | Miyahara | |
| 7,097,209 B2 | 8/2006 | Unger et al. | |
| 7,261,707 B2 | 8/2007 | Frezza et al. | |
| 7,306,584 B2 | 12/2007 | Wessman et al. | |
| 7,316,425 B2 * | 1/2008 | Poder | F16L 37/0841 285/305 |
| 7,326,194 B2 | 2/2008 | Zinger et al. | |
| 7,350,535 B2 | 4/2008 | Liepold et al. | |
| 7,354,427 B2 | 4/2008 | Fangrow | |
| 7,452,349 B2 | 11/2008 | Miyahara | |
| 7,547,300 B2 | 6/2009 | Fangrow | |
| 7,628,772 B2 | 12/2009 | McConnell et al. | |
| 7,648,491 B2 | 1/2010 | Rogers | |
| 7,658,734 B2 | 2/2010 | Adair et al. | |
| 7,703,486 B2 | 4/2010 | Costanzo | |
| 7,743,799 B2 | 6/2010 | Mosler et al. | |
| 7,744,581 B2 | 6/2010 | Wallen et al. | |
| 7,758,560 B2 | 7/2010 | Connell et al. | |
| 7,803,140 B2 | 9/2010 | Fangrow, Jr. | |
| 7,867,215 B2 | 1/2011 | Akerlund et al. | |
| 7,879,018 B2 | 2/2011 | Zinger et al. | |
| 7,900,659 B2 | 3/2011 | Whitley et al. | |
| 7,927,316 B2 | 4/2011 | Proulx et al. | |
| 7,942,860 B2 | 5/2011 | Horppu | |
| 7,975,733 B2 | 7/2011 | Horppu et al. | |
| 8,066,688 B2 * | 11/2011 | Zinger | A61J 1/2096 604/411 |
| 8,096,525 B2 | 1/2012 | Ryan | |
| 8,122,923 B2 | 2/2012 | Kraus et al. | |
| 8,123,738 B2 | 2/2012 | Vaillancourt | |
| 8,137,332 B2 | 3/2012 | Pipelka | |
| 8,167,863 B2 | 5/2012 | Yow | |
| 8,177,768 B2 | 5/2012 | Leinsing | |
| 8,196,614 B2 | 6/2012 | Kriheli | |
| 8,206,367 B2 | 6/2012 | Warren et al. | |
| 8,211,069 B2 | 7/2012 | Fangrow, Jr. | |
| 8,226,628 B2 | 7/2012 | Muramatsu et al. | |
| 8,251,346 B2 * | 8/2012 | Stroup | A61M 39/26 251/149.5 |
| 8,257,286 B2 | 9/2012 | Meyer et al. | |
| 8,267,127 B2 | 9/2012 | Kriheli | |
| 8,277,424 B2 | 10/2012 | Pan | |
| 8,317,741 B2 | 11/2012 | Kraushaar | |
| 8,317,743 B2 | 11/2012 | Denenburg | |
| 8,398,607 B2 | 3/2013 | Fangrow, Jr. | |
| 8,403,905 B2 | 3/2013 | Yow | |
| 8,425,487 B2 | 4/2013 | Beiriger et al. | |
| 8,435,210 B2 * | 5/2013 | Zinger | A61J 1/2096 604/82 |
| 8,449,521 B2 | 5/2013 | Thorne, Jr. et al. | |
| 8,454,579 B2 | 6/2013 | Fangrow, Jr. | |
| 8,647,326 B2 * | 2/2014 | Solomon | A61M 39/20 604/533 |
| 10,151,413 B2 * | 12/2018 | Blake | F16L 37/0841 |
| 2003/0070726 A1 | 4/2003 | Andreasson et al. | |
| 2004/0215147 A1 | 10/2004 | Wessman et al. | |
| 2005/0065495 A1 | 3/2005 | Lambaux | |
| 2005/0182383 A1 | 8/2005 | Wallen | |
| 2005/0215976 A1 | 9/2005 | Wallen | |
| 2006/0082145 A1 * | 4/2006 | Steveley | F16L 37/144 285/305 |
| 2006/0128180 A1 * | 6/2006 | Gammons | F16L 37/0841 439/76.1 |
| 2007/0079894 A1 | 4/2007 | Kraus et al. | |
| 2007/0126232 A1 * | 6/2007 | Campagna | F16L 37/144 285/319 |
| 2008/0045919 A1 | 2/2008 | Jakob et al. | |
| 2008/0218998 A1 * | 9/2008 | Quest | G01M 3/38 362/230 |
| 2008/0249479 A1 | 10/2008 | Zinger et al. | |
| 2008/0287867 A1 * | 11/2008 | Yow | A61M 5/162 604/86 |
| 2008/0287914 A1 | 11/2008 | Wyatt et al. | |
| 2009/0159485 A1 | 6/2009 | Jakob et al. | |
| 2010/0019487 A1 * | 1/2010 | deCler | F16L 37/0841 285/308 |
| 2010/0042942 A1 * | 2/2010 | Vasilevsky | G06F 9/45533 715/764 |
| 2010/0099487 A1 | 4/2010 | Canterbury et al. | |
| 2010/0179506 A1 | 7/2010 | Shemesh et al. | |
| 2010/0217226 A1 | 8/2010 | Shemesh et al. | |
| 2010/0241088 A1 * | 9/2010 | Ranalletta | A61J 1/2089 604/264 |
| 2011/0004183 A1 | 1/2011 | Carrez et al. | |
| 2011/0062703 A1 | 3/2011 | Lopez et al. | |
| 2011/0074148 A1 | 3/2011 | Imai | |
| 2011/0106046 A1 * | 5/2011 | Hiranuma | A61J 1/2096 604/414 |
| 2011/0257621 A1 | 10/2011 | Fangrow | |
| 2011/0291406 A1 | 12/2011 | Kraft et al. | |
| 2012/0035580 A1 | 2/2012 | Fangrow | |
| 2012/0046636 A1 | 2/2012 | Kriheli | |
| 2012/0123381 A1 | 5/2012 | Kraus et al. | |
| 2012/0179128 A1 * | 7/2012 | Takemoto | A61M 5/162 604/414 |

(56) References Cited

U.S. PATENT DOCUMENTS

| | | |
|---|---|---|
| 2012/0192968 A1 | 8/2012 | Bonnal et al. |
| 2012/0192976 A1 | 8/2012 | Rahimy et al. |
| 2012/0203193 A1* | 8/2012 | Rogers ............... A61M 39/26 604/403 |
| 2012/0265163 A1 | 10/2012 | Cheng et al. |
| 2012/0279884 A1 | 11/2012 | Tennican et al. |
| 2012/0316536 A1* | 12/2012 | Carrez ............. A61M 39/1011 604/535 |
| 2013/0006200 A1* | 1/2013 | Ellstrom ............... A61J 1/2089 604/263 |
| 2013/0006211 A1 | 1/2013 | Takemoto |
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079730 A1* | 3/2013 | Mosler ............... A61M 39/10 604/244 |
| 2013/0079744 A1 | 3/2013 | Okiyama et al. |
| 2013/0197485 A1* | 8/2013 | Gardner ............ A61M 39/162 604/533 |
| 2013/0300108 A1* | 11/2013 | Frick ................. F16L 37/0841 285/319 |
| 2014/0034185 A1* | 2/2014 | Mueller ............... A61J 1/2089 141/1 |
| 2015/0096928 A1* | 4/2015 | Adey ..................... B03C 1/286 210/222 |

FOREIGN PATENT DOCUMENTS

| | | |
|---|---|---|
| JP | H04506555 A | 11/1992 |
| WO | 2005011781 A1 | 2/2005 |
| WO | 2006103074 A1 | 10/2006 |
| WO | 2007015233 A1 | 2/2007 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |

* cited by examiner

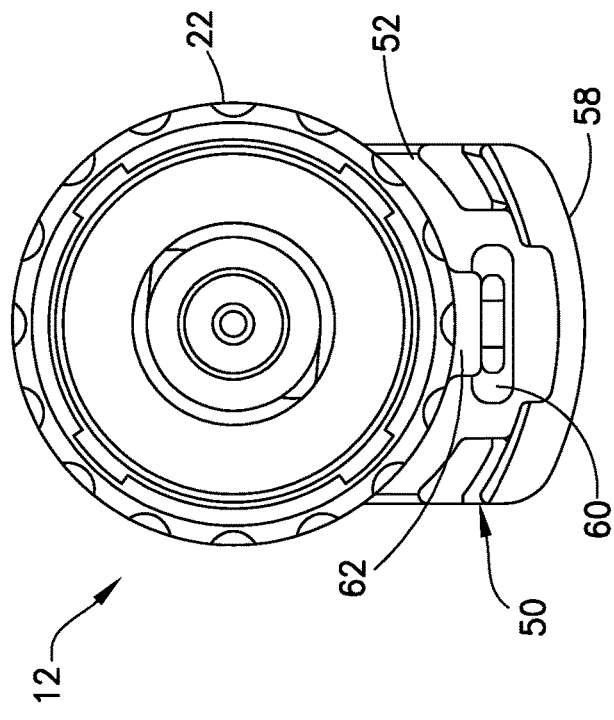
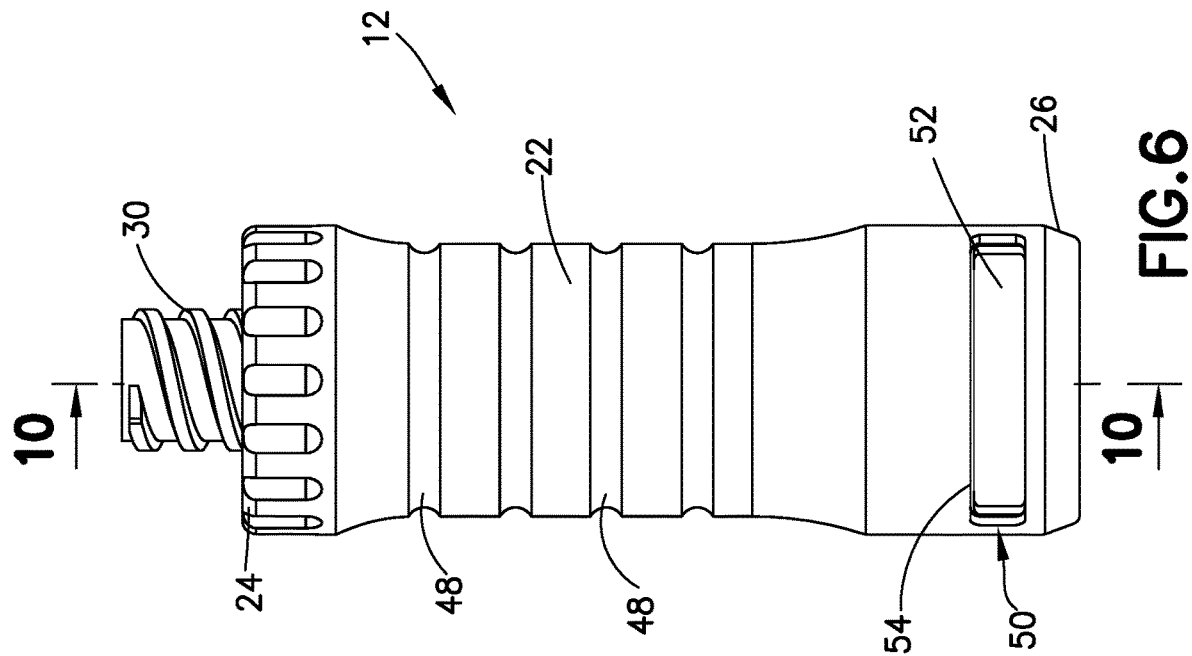

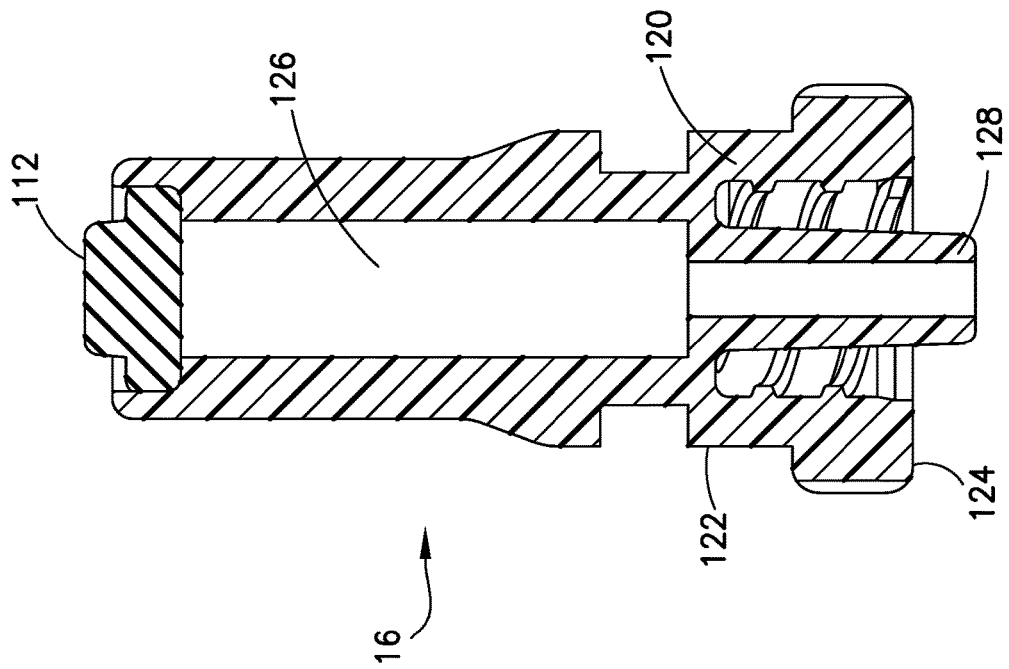
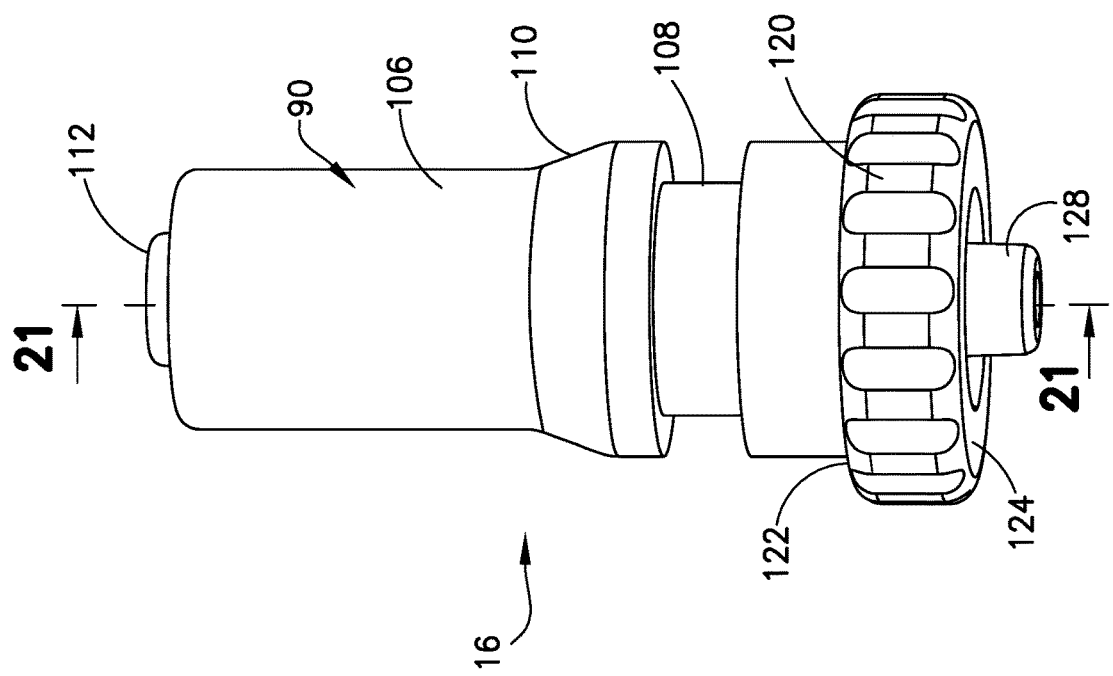

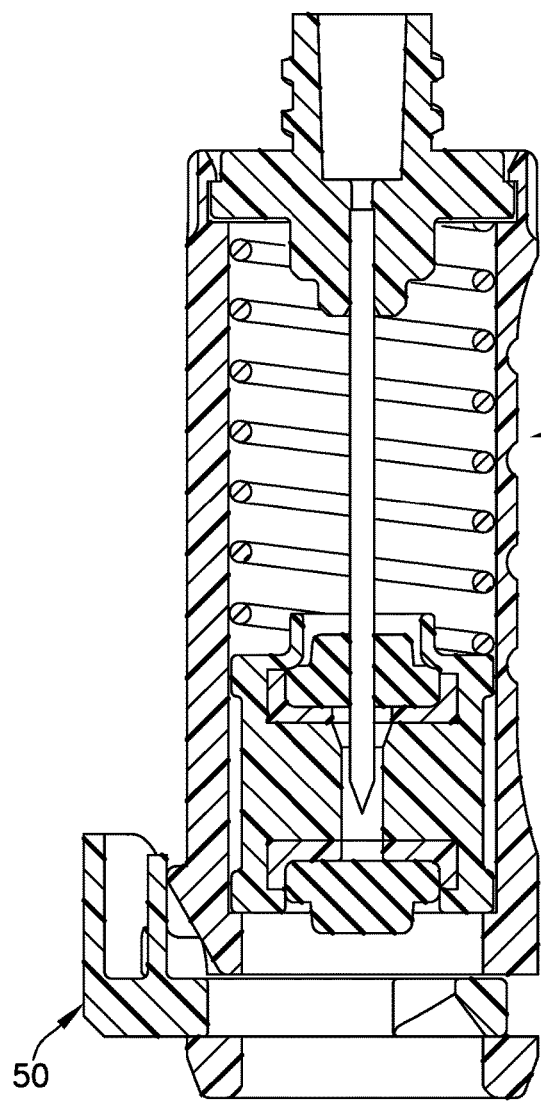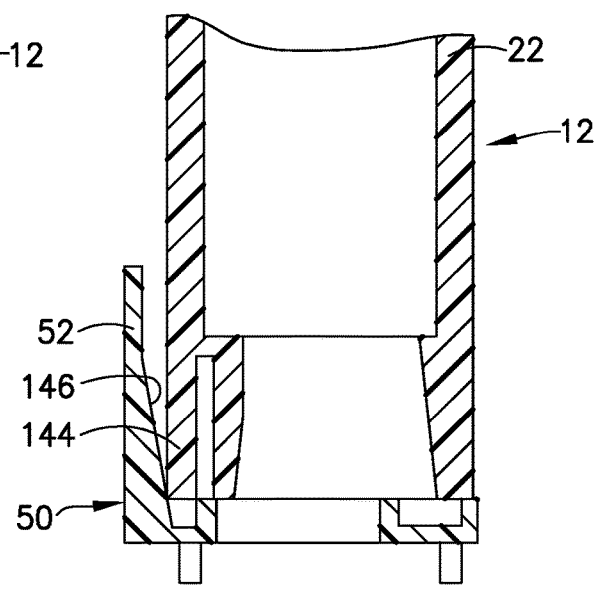
FIG.27
FIG.28

SYSTEM FOR CLOSED TRANSFER OF FLUIDS HAVING CONNECTOR

CROSS-REFERENCE TO RELATED APPLICATION

This application is a continuation of U.S. patent application Ser. No. 14/532,188, filed Nov. 4, 2014, which claims priority to U.S. Provisional Application Ser. No. 61/900,623, filed Nov. 6, 2013, each of which are hereby incorporated by reference in their entirety.

BACKGROUND OF THE INVENTION

1. Field of the Disclosure

The present disclosure relates generally to a system for the closed transfer of fluids. More particularly, the present disclosure relates to a system that provides leak-proof sealing and pressure equalization during engagement of a cannula with a vial, during transfer of a substance from a vial chamber to a barrel chamber via the cannula, and during disengagement of the cannula from the vial.

2. Description of the Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists.

SUMMARY OF THE INVENTION

In one aspect, a system, such as a system for the closed transfer of fluids, includes a syringe adapter having a first end and a second end with the first end of the syringe adapter configured to be connected to a first container and the second end of the syringe adapter including a lock member having an open position and a closed position. The system also includes a vial adapter having a first end and a second end with the second end of the vial adapter configured to be connected to a second container and the first end of the vial adapter having a locking surface. The syringe adapter is configured to be mated with the vial adapter when the lock member is in the open position and is configured to be locked to the vial adapter when the lock member is in the closed position and positioned adjacent to the locking surface. The lock member includes at least one projection that extends radially outward. The syringe adapter has at least one corresponding projection configured to engage the at least one projection of the lock member to retain the lock member to the syringe adapter.

The system may also include a patient connector having a first end and a second end and defining a passageway with the first end of the patient connector including a locking surface configured to engage the lock member of the syringe adapter and the second end of the patient connector configured to be secured to a patient IV line. The syringe adapter may comprise a body and a seal arrangement positioned within the body with the seal arrangement having at least one membrane and configured to move within the body of the syringe adapter. The vial adapter may comprise a pressure equalization arrangement and a spike. The body of the syringe adapter may define an opening extending transversely relative to a longitudinal axis of the syringe adapter that receives the lock member with the lock member configured to move relative to the body of the syringe adapter between the open position and the closed position. The lock member may include a biasing member that is configured to bias the lock member towards the closed position. The lock member may include a lead-in surface that is configured to contact the second end of the vial adapter and move the lock member from the closed position to the open position when the syringe adapter is mated with the vial adapter.

The biasing member of the lock member may comprise a cantilever spring with the body of the syringe adapter defining a cam surface configured to engage the cantilever spring of the lock member. The cantilever spring may extend in an axial direction with the cam surface extending radially outward from the body of the syringe adapter. The at least one projection of the lock member may comprise a pair of projections positioned on opposite sides of the lock member, and the at least one corresponding projection of the syringe adapter may comprise a pair of corresponding projections configured to engage the pair of projections of the lock member. The lock member may be annular and received within an opening defined by the body of the syringe adapter with the opening of the syringe adapter extending transversely relative to a longitudinal axis of the syringe adapter. The lock member may include a button that is configured to be engaged by a hand of a user of the syringe adapter to move the lock member from the closed position to the open position. The seal arrangement may comprise a membrane carrier having a membrane with the first end of the vial adapter having a membrane configured to engage the membrane of the membrane carrier. The membrane carrier may be biased toward the second end of the syringe adapter via biasing member. The first end of the syringe adapter may include a female luer connector configured to be secured to a syringe.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein:

FIG. 6 is a rear view of the syringe adapter of FIG. 3 according to one aspect of the present invention.

FIG. 7 is a top view of the syringe adapter of FIG. 3 according to one aspect of the present invention.

FIG. 20 is a front perspective view of a patient connector of the system of FIG. 1 according to one aspect of the present invention.

FIG. 21 is a cross-sectional view of the patient connector taken along line 21-21 in FIG. 20 according to one aspect of the present invention.

FIG. 27 is a cross-sectional view of a syringe adapter of the system of FIG. 25 according to one aspect of the present invention.

FIG. 28 is a cross-sectional view of a syringe adapter according to a further aspect of the present invention.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
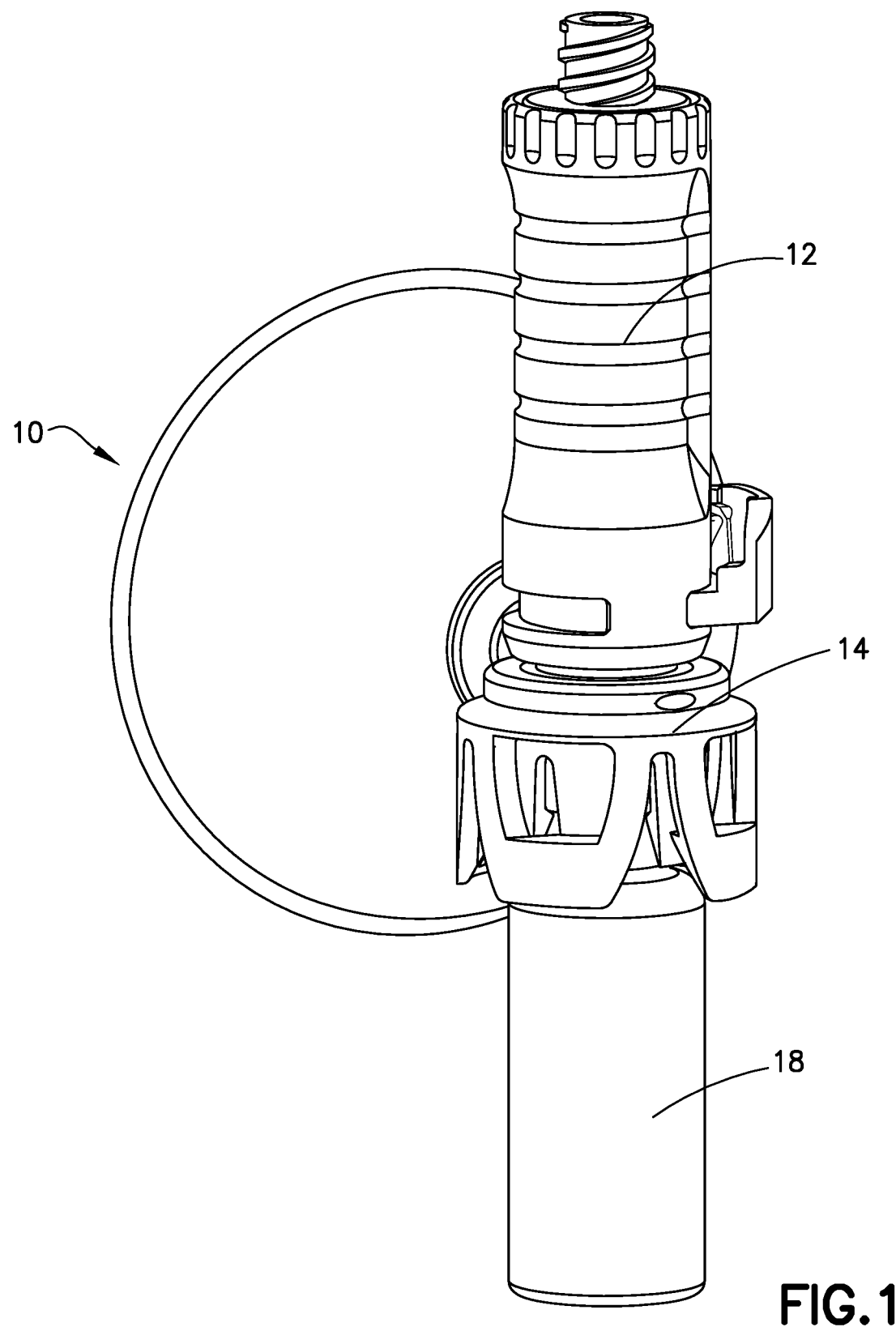
FIG. 1 is a perspective view of a system according to one aspect of the present invention.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

In the following discussion, "distal" refers to a direction generally toward an end of a system adapted for contact with a container, such as a vial, and "proximal" refers to the opposite direction of distal, i.e., away from the end of a system adapted for contact with the container. For purposes of this disclosure, the above-mentioned references are used in the description of the components of a system in accordance with the present disclosure.

Figure 2:
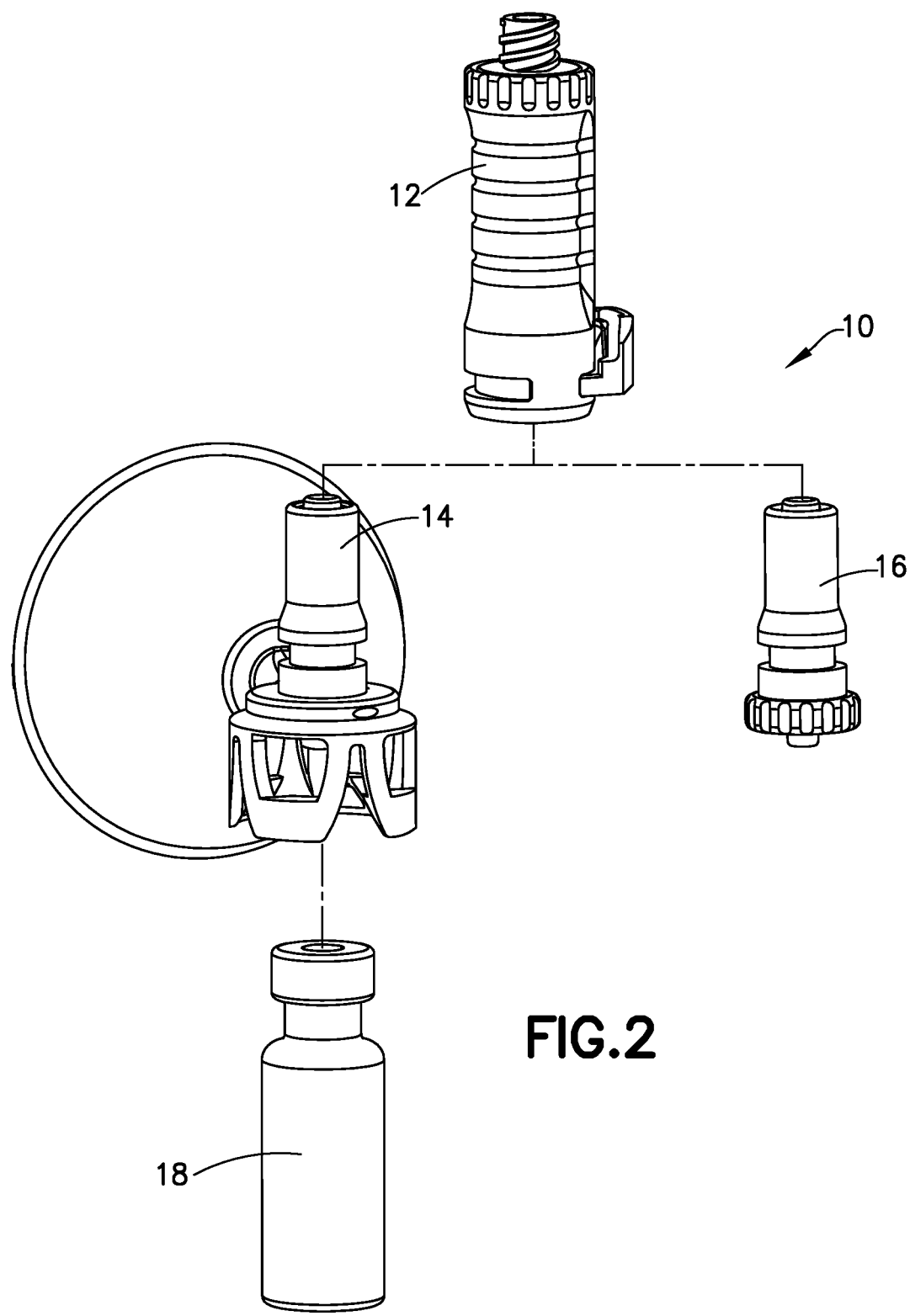
FIG. 2 is an exploded, perspective view of the system of FIG. 1 according to one aspect of the present invention.
Figure 3:
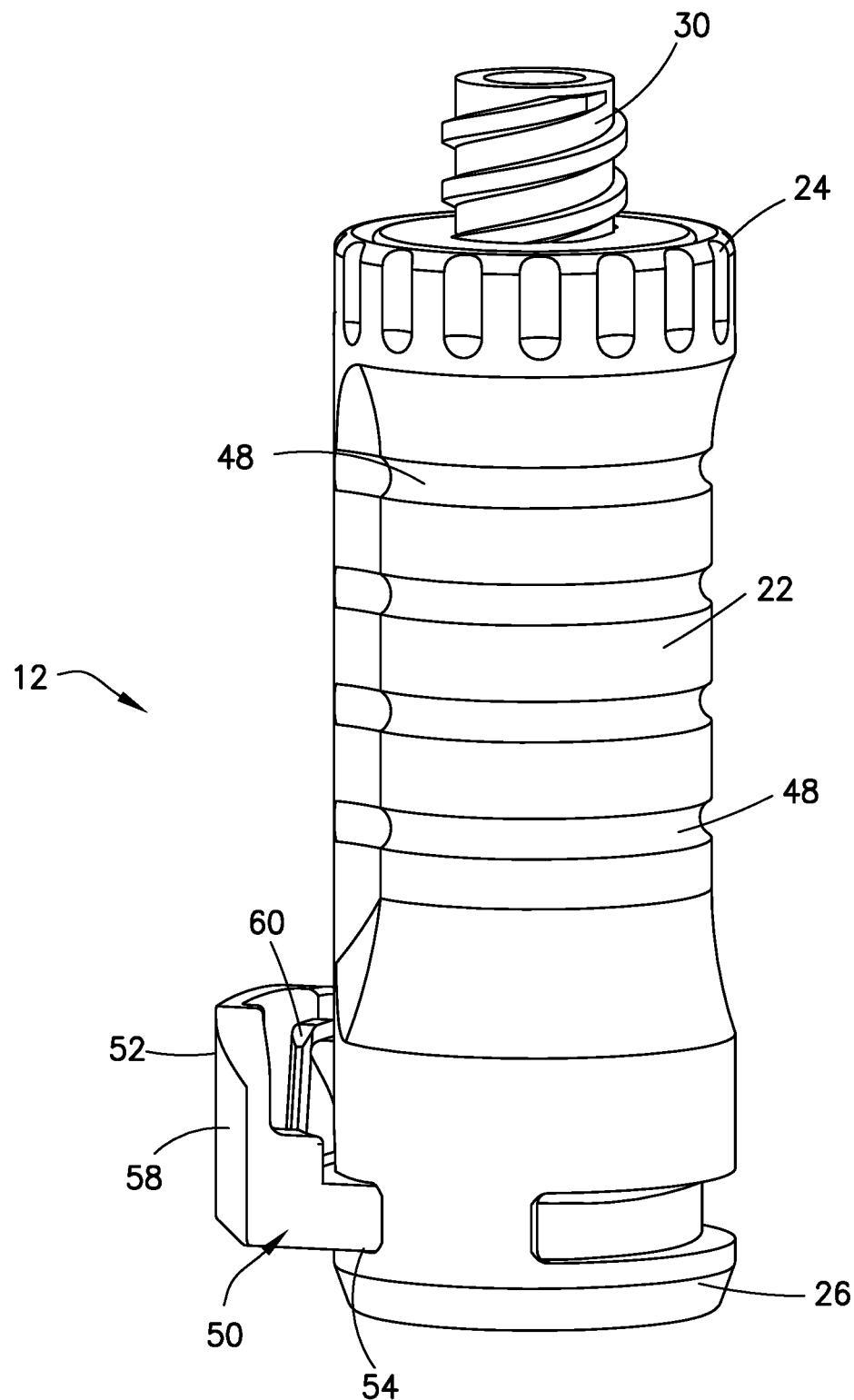
FIG. 3 is a perspective view of a syringe adapter of the system of FIG. 1 according to one aspect of the present invention.

Referring to FIGS. 1 and 2, one aspect of a system 10 for the closed transfer of fluids includes a syringe adapter 12, a vial adapter 14, and a patient connector 16. The system 10 provides substantially leak-proof sealing during transfer of a fluid from a first container 18, such as a vial, to a second container (not shown), such as a syringe, IV bag, or patient IV line. The leak-proof sealing of the system 10 substantially prevents leakage of both air and liquid during use of the system 10. Although not shown, the system may further include an IV bag adapter as well as other components typically utilized in closed system transfer devices, such as infusion lines and extension sets Referring to FIGS. 3-14, one aspect of the syringe adapter 12 includes a body 22 having a first end 24 and a second end 26 and defining interior space 28. The first end 24 of the body 22 of the syringe adapter 12 includes a syringe attachment 30, such as a female luer connector, that defines a passageway 32. Although a female luer connector is shown for connection with a corresponding male luer connector of a syringe (not shown), other suitable connection arrangements may be utilized for connection to a syringe, container, or any other medical device. A cannula 34 having a distal end 36 is secured to the syringe attachment 30 and in fluid communication with the passageway 32 of the syringe attachment 30. The syringe adapter 12 further includes a seal arrangement 38 positioned within the body 22 of the syringe adapter 12. The seal arrangement 38 includes a membrane carrier 40 that receives a first membrane 42 and a second membrane 44 spaced from the first membrane 42. The seal arrangement 38 further includes a biasing member 46, such as a compression spring, that engages the membrane carrier 40 and the syringe attachment 30 (or the body) and is configured to bias the membrane carrier 40 toward the second end 26 of the syringe adapter 12. The body 22 of the syringe adapter 12 may include structure to enhance gripping of the syringe adapter 12 by a user. In particular, the body 22 of the syringe adapter 12 includes a plurality of annular grooves 48 that extend around the circumference of the body 22 of the syringe adapter 12, which enhances the ability of a user to grip the syringe adapter 12. The body 22 of the syringe adapter 12 also includes a plurality of recessed portions adjacent to the first end 24 of the syringe adapter 12 that extend in a longitudinal direction and around the circumference of the body 22. Additional or alternative grip structures and surfaces may be provided to assist a user in gripping the body 22 of the syringe adapter 12.

Figure 10:
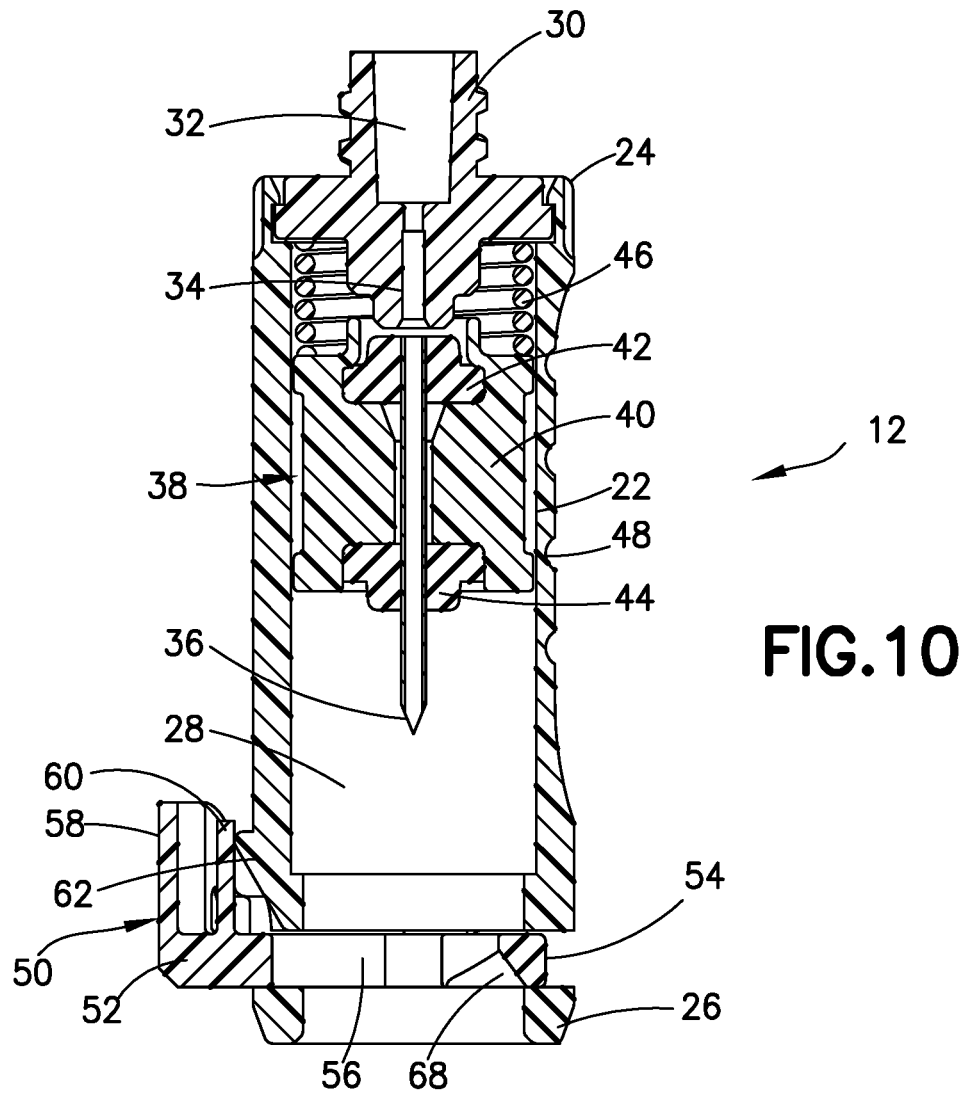
FIG. 10 is a cross-sectional view of the syringe adapter along line 10-10 in FIG. 6 according to one aspect of the present invention.

Upon engagement of the second membrane 44 by a corresponding membrane during use, the membrane carrier 40 is configured to move towards the first end 24 of the syringe adapter 12 such that the distal end 36 of the cannula 34 pierces the second membrane 44 to place the syringe adapter 12 in fluid communication with the corresponding device secured to the syringe adapter 12, as discussed below in more detail. After the second membrane 44 is disengaged from the corresponding membrane, the membrane carrier 40 is biased back to its original position thereby positioning the distal end 36 of the cannula 34 between the first and second membranes 42, 44. In FIG. 10, the membrane carrier 40 is shown after being moved toward the first end 24 of the syringe adapter 12 with the distal end 36 of the cannula 34 piercing the second membrane 44. However, the membrane carrier 40 will only be in the position shown in FIG. 10 after engagement with the vial adapter 14 or the patient connector 16.

Such an arrangement shields the distal end 36 of the cannula 34 to prevent accidental needle sticks and also prevents the leakage of any fluid during transfer of fluids when using the syringe adapter 12. Although the biasing member 46 is shown as a compression spring, any other suitable biasing arrangement may be utilized to bias the membrane carrier 40 towards the second end 26 of the syringe adapter 12. Further, although the seal arrangement 38 includes first and second membranes 42, 44 and the membrane carrier 40, any other suitable arrangement for sealing and shielding the cannula 34 during use may be utilized.

Referring again to FIGS. 3-14, the second end 26 of the syringe adapter 12 includes a first connection interface 50 that includes a lock member 52 that is received within a transverse opening 54 in the body 22 of the syringe adapter 12. The lock member 52 is configured to move between a closed position and an open position. The lock member 52 defines a central opening 56 and includes a button 58 that is configured to be engaged by a hand of a user or operator of the syringe adapter 12. The lock member 52 further includes a cantilever spring 60 that extends in a longitudinal direction of the syringe adapter 12. The lock member 52 is configured to engage a cam surface 62 that extends radially outward from the body 22 of the syringe adapter 12. In particular, the lock member 52 is configured to be provided in the closed position, where a portion of the lock member 52 adjacent to the central opening 56 of the lock member 52 is positioned within the interior space 28 of the syringe adapter 12 when no external forces are applied to the lock member 52. When the lock member 52 is moved to the open position where the central opening 56 of the lock member 52 is aligned with the interior space 28 of the syringe adapter 12 or does not create an interference or barrier to objects being inserted into the interior space 28, as discussed in more detail below, the cantilever spring 60 engages the cam surface 62 to create a biasing force that urges the lock member 52 back towards the closed position. Accordingly, when the lock member 52 is moved to the open position, the lock member 52 will be urged back to the closed position when the external force acting on the lock member 52 is released. Although the lock member 52 is shown with the cantilever spring 60, any other suitable biasing member may be provided including, but not limited to, compression springs, extension springs, elastomeric material, etc.

Figure 5:
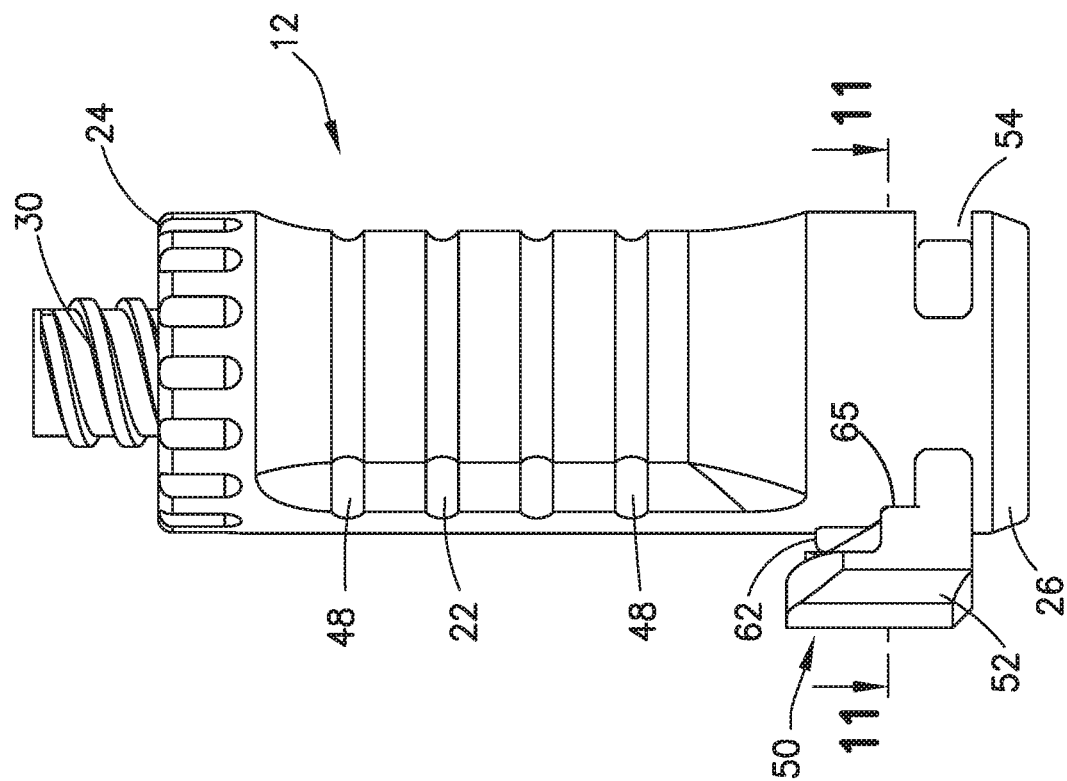
FIG. 5 is a left side view of the syringe adapter of FIG. 3 according to one aspect of the present invention.
Figure 4:
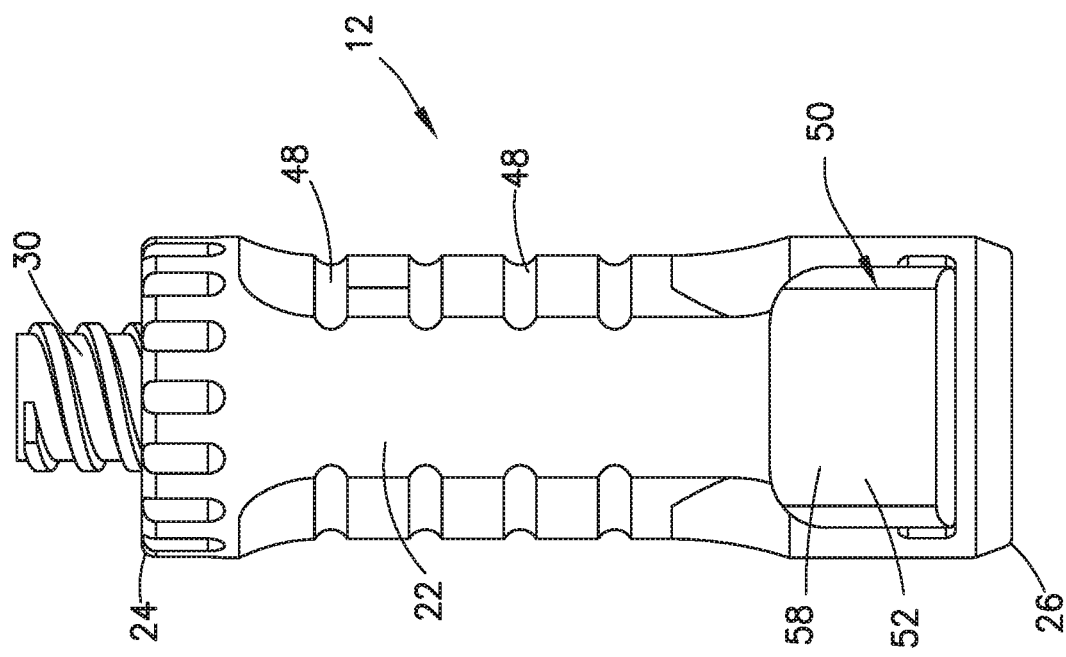
FIG. 4 is a front view of the syringe adapter of FIG. 3 according to one aspect of the present invention.
Figure 9:
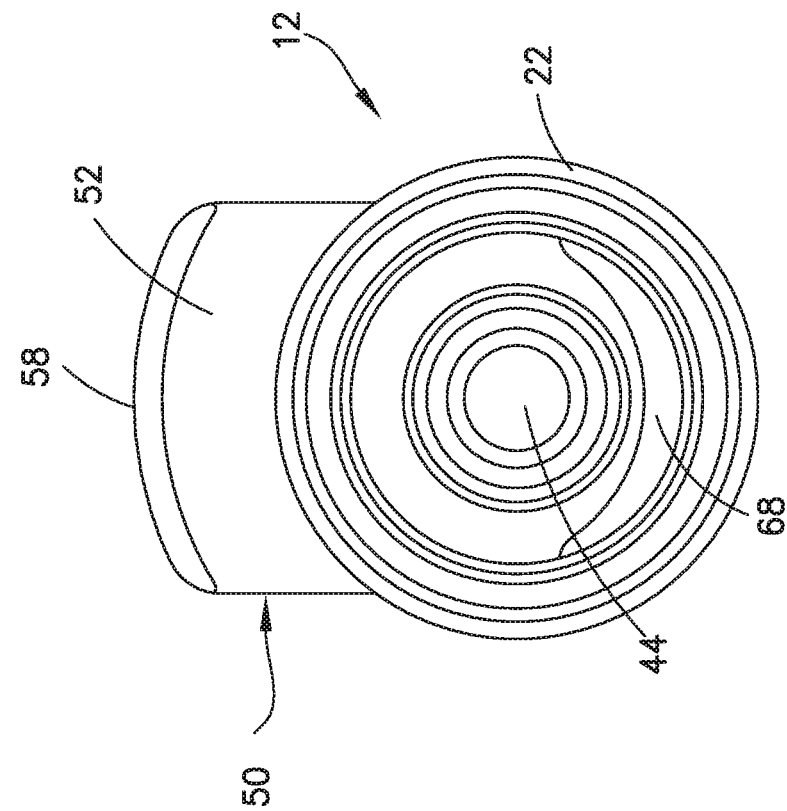
FIG. 9 is a bottom view of the syringe adapter of FIG. 3 according to one aspect of the present invention.
Figure 8:
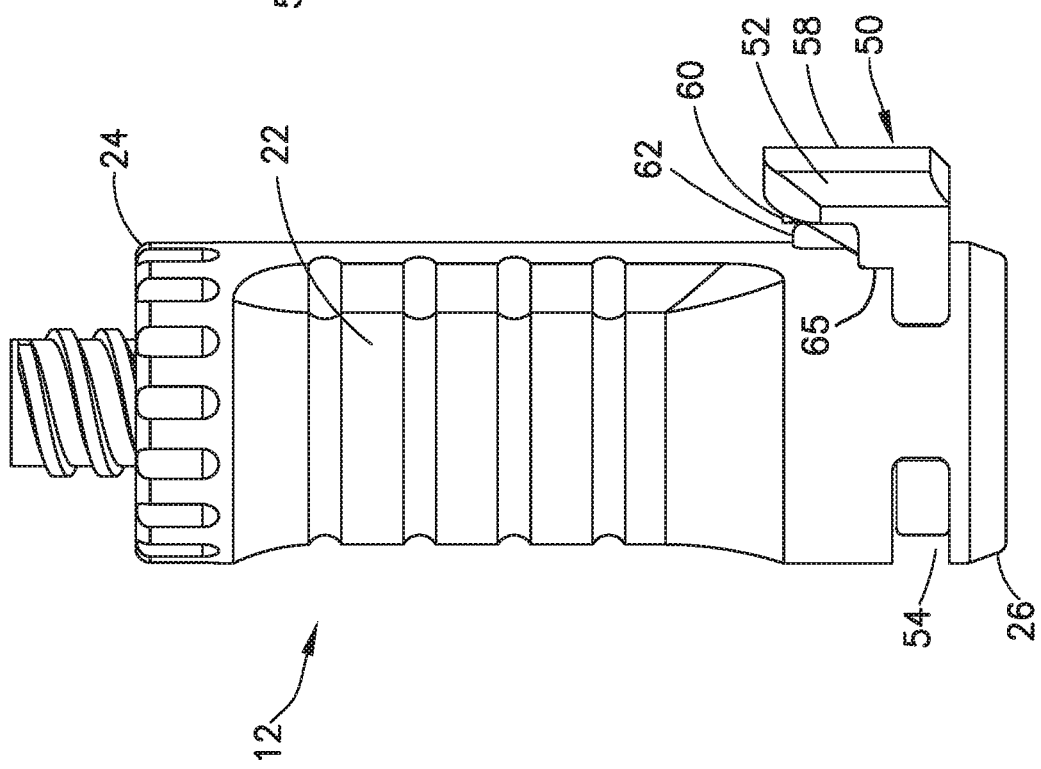
FIG. 8 is a right side view of the syringe adapter of FIG. 3 according to one aspect of the present invention.
Figure 11:
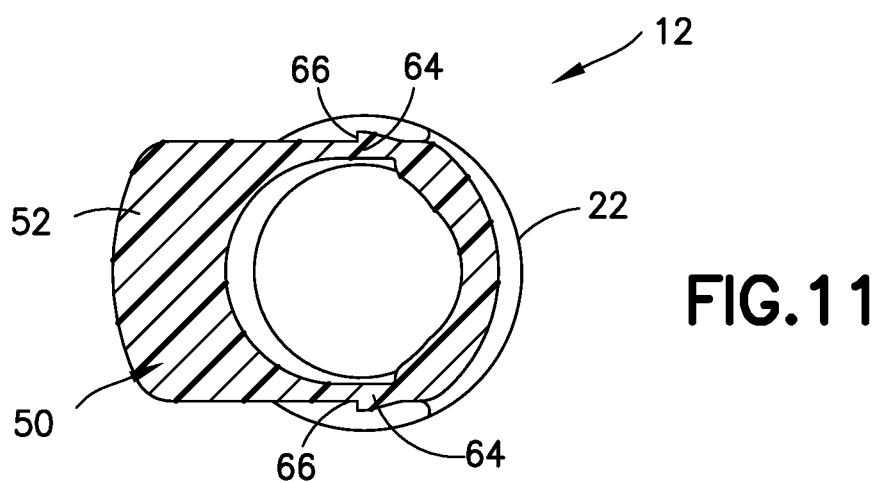
FIG. 11 is a cross-sectional view of the syringe adapter along line 11-11 in FIG. 5 according to one aspect of the present invention.
Figure 13:
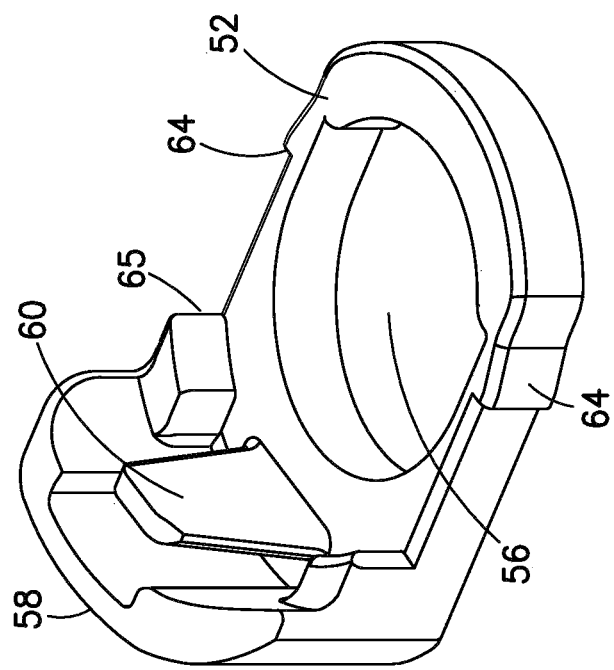
FIG. 13 is a top perspective view of a lock member of the syringe adapter of FIG. 3 according to one aspect of the present invention.
Figure 12:
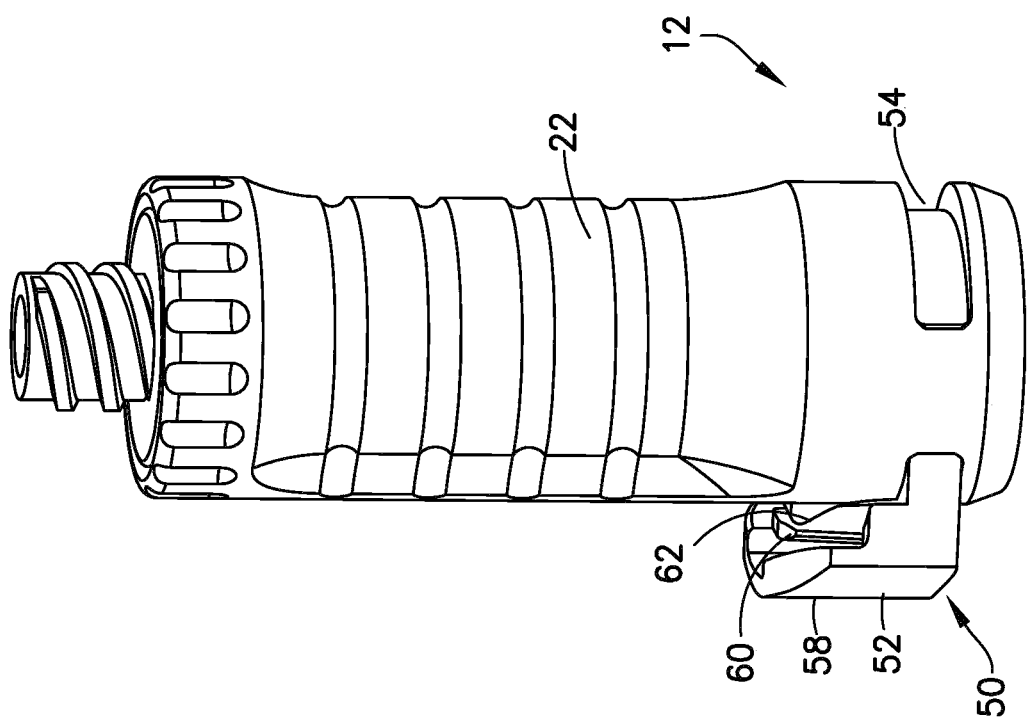
FIG. 12 is an enlarged perspective view of the syringe adapter of FIG. 3 according to one aspect of the present invention.

Referring to FIG. 11, the lock member 52 further includes a pair of projections 64 that extend radially outward from the lock member 52. The pair of projections 64 is configured to engage corresponding projections 66 provided on the body 22 of the syringe adapter 12 to retain the lock member 52 to the body 22 of the syringe adapter 12. In other words, the projections 64 of the lock member 52 are configured to engage the projections 66 of the body 22 of the syringe adapter 12 to prevent the lock member 52 from being disconnected and removed from the transverse opening 54 of the body 22 of the syringe adapter 12. Referring to FIG. 13, the lock member 52 further includes a pair of projections 65 that extend axially upward from the lock member 52. The pair of axially extending projections 65 may further include a curved portion that engages the external surface of the syringe adapter when the lock member is in the open position, as shown in FIGS. 5 and 8.

Figure 14:
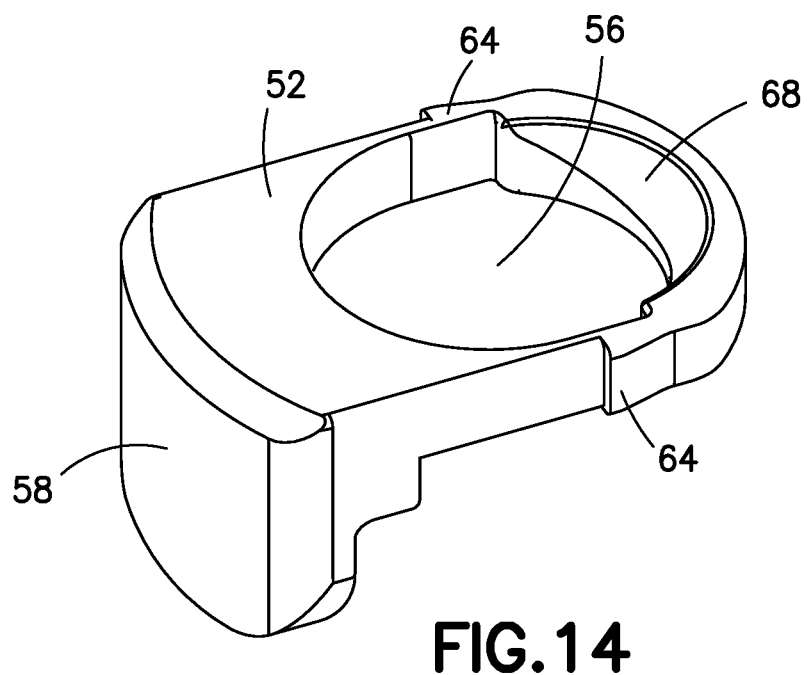
FIG. 14 is bottom perspective view of the lock member shown in FIG. 13 according to one aspect of the present invention.
Figure 15:
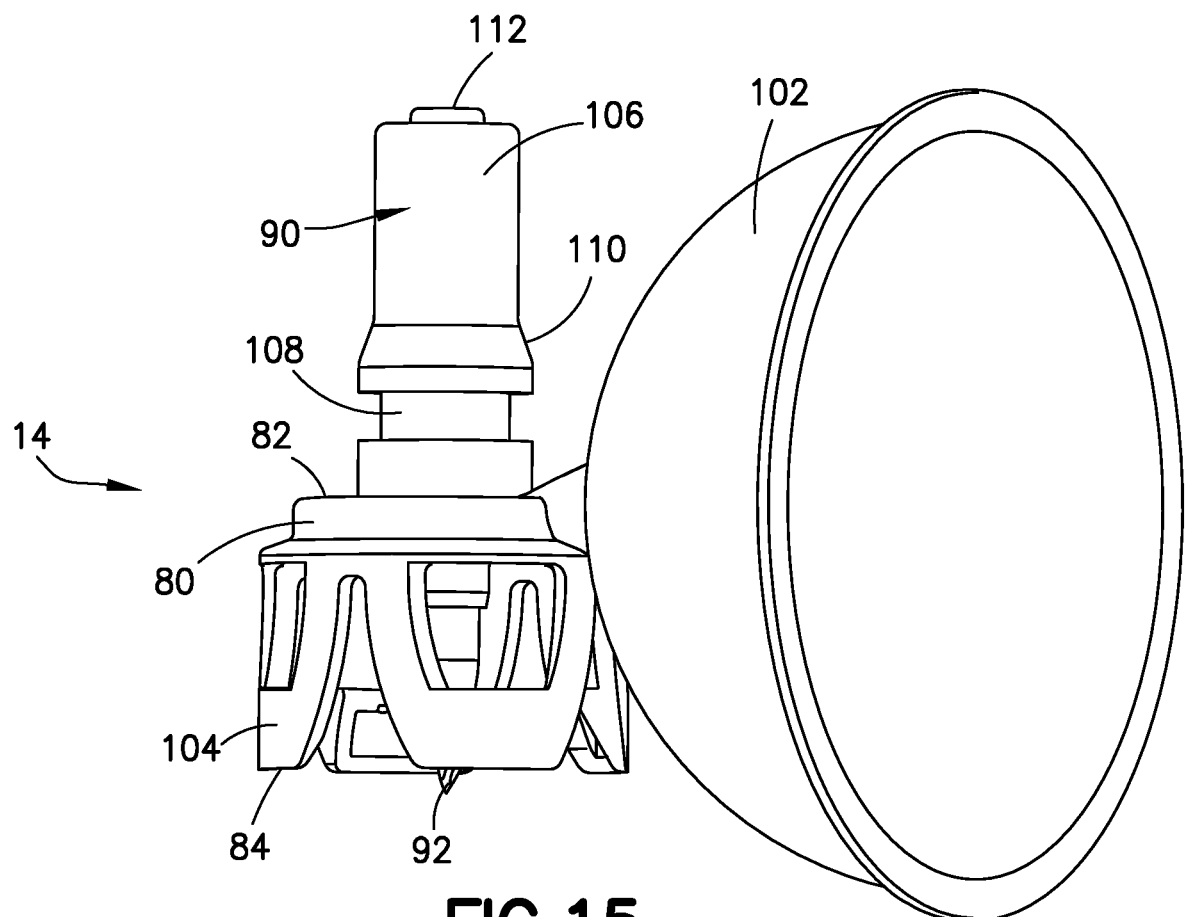
FIG. 15 is a front perspective view of a vial adapter of the system of FIG. 1 according to one aspect of the present invention.
Figure 16:
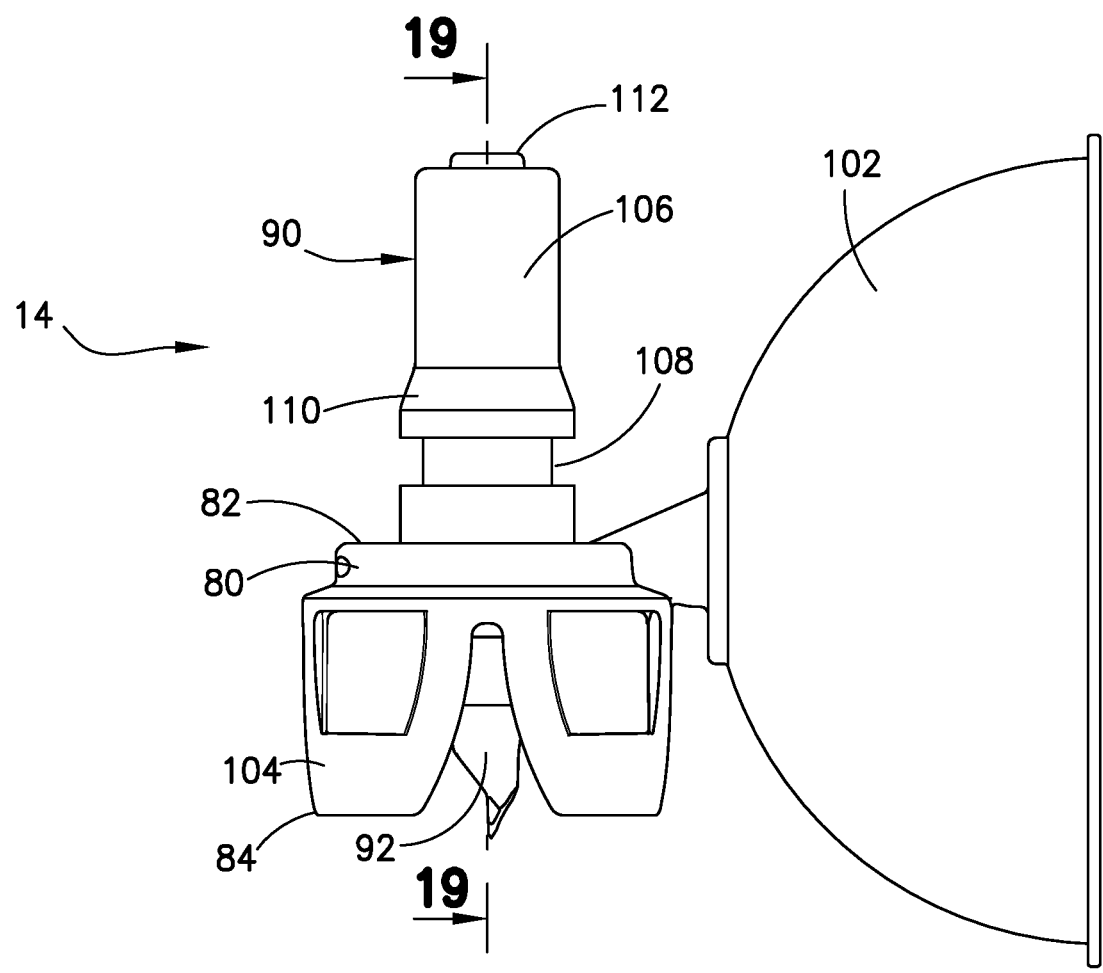
FIG. 16 is a front view of the vial adapter of FIG. 15 according to one aspect of the present invention.
Figure 17:
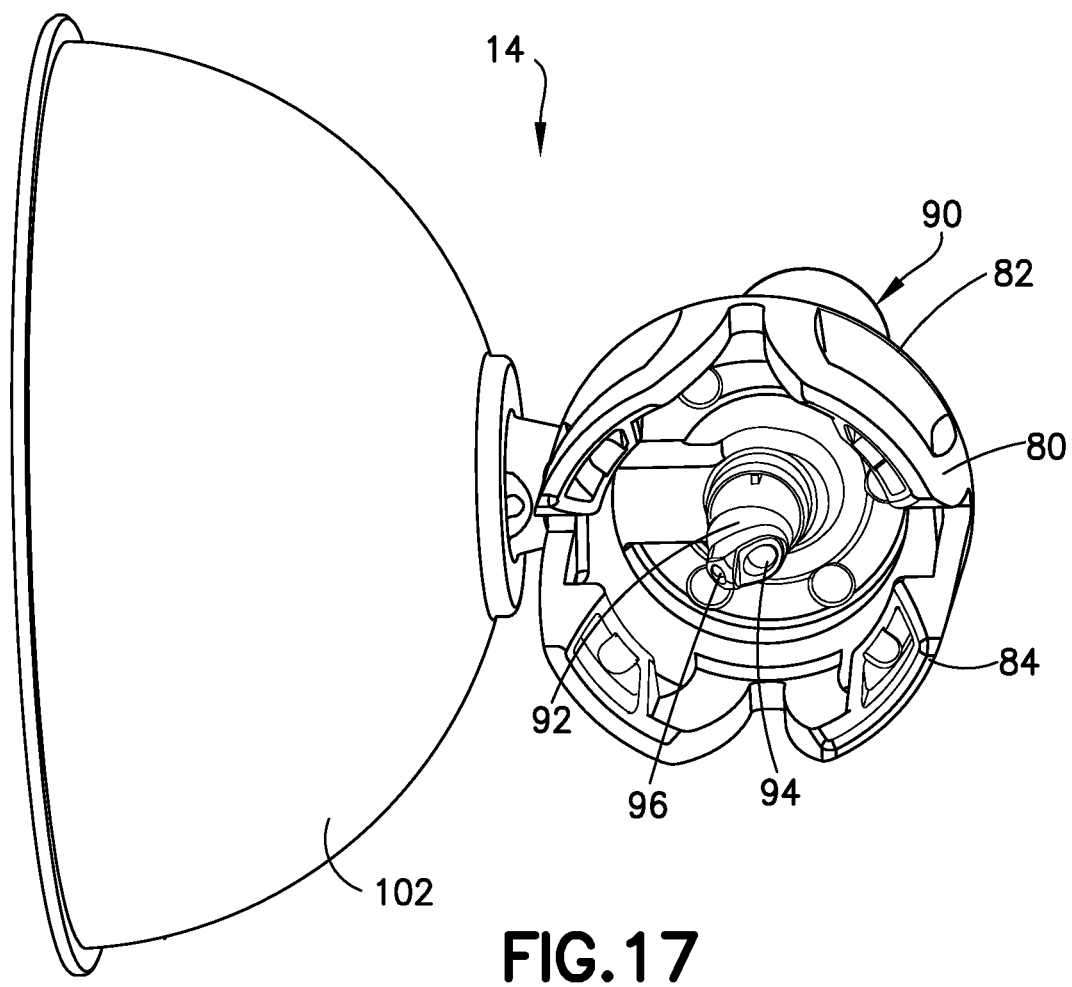
FIG. 17 is a bottom perspective view of the vial adapter of FIG. 15 according to one aspect of the present invention.
Figure 18:
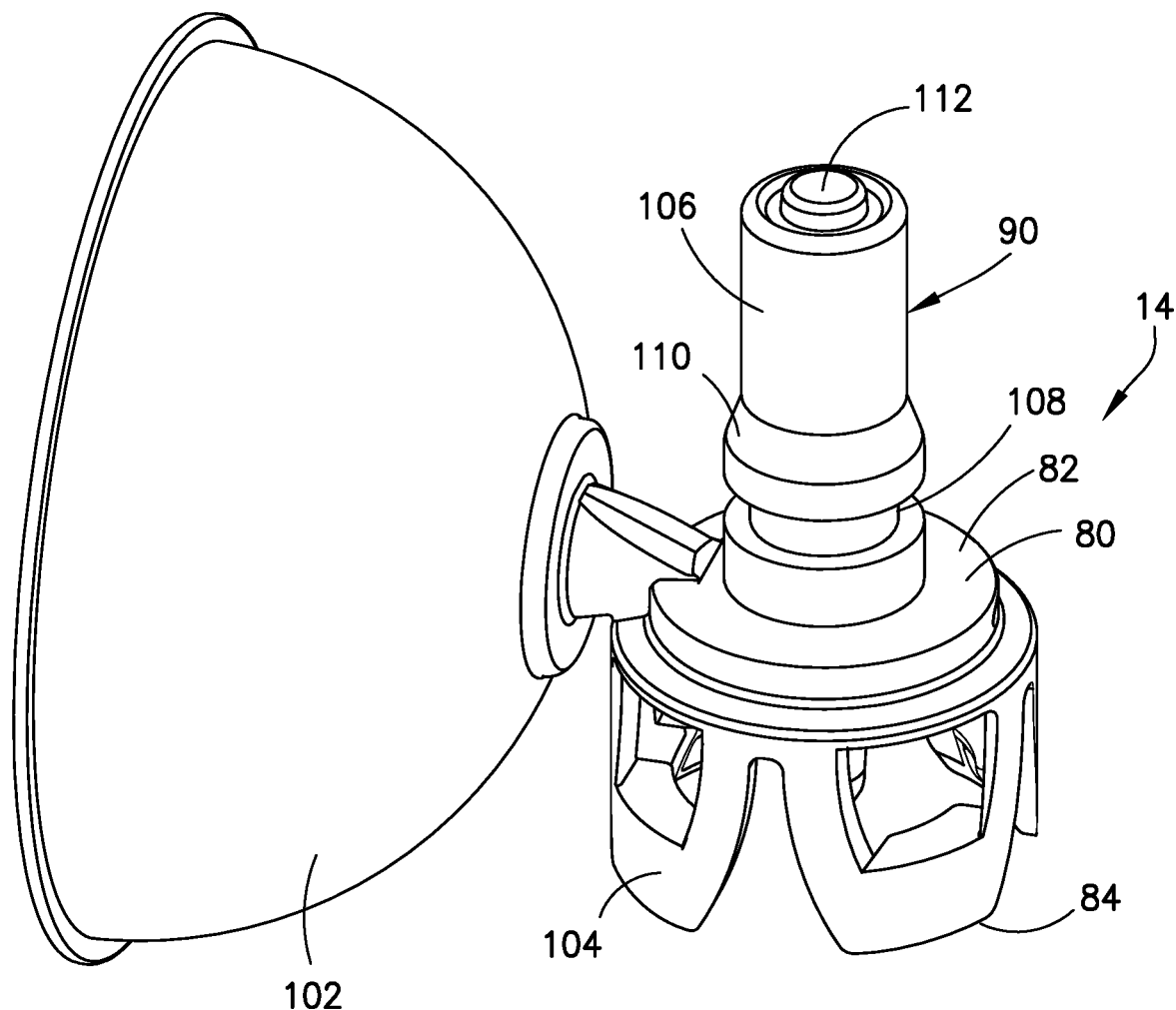
FIG. 18 is a top perspective view of the vial adapter of FIG. 15 according to one aspect of the present invention.
Figure 19:
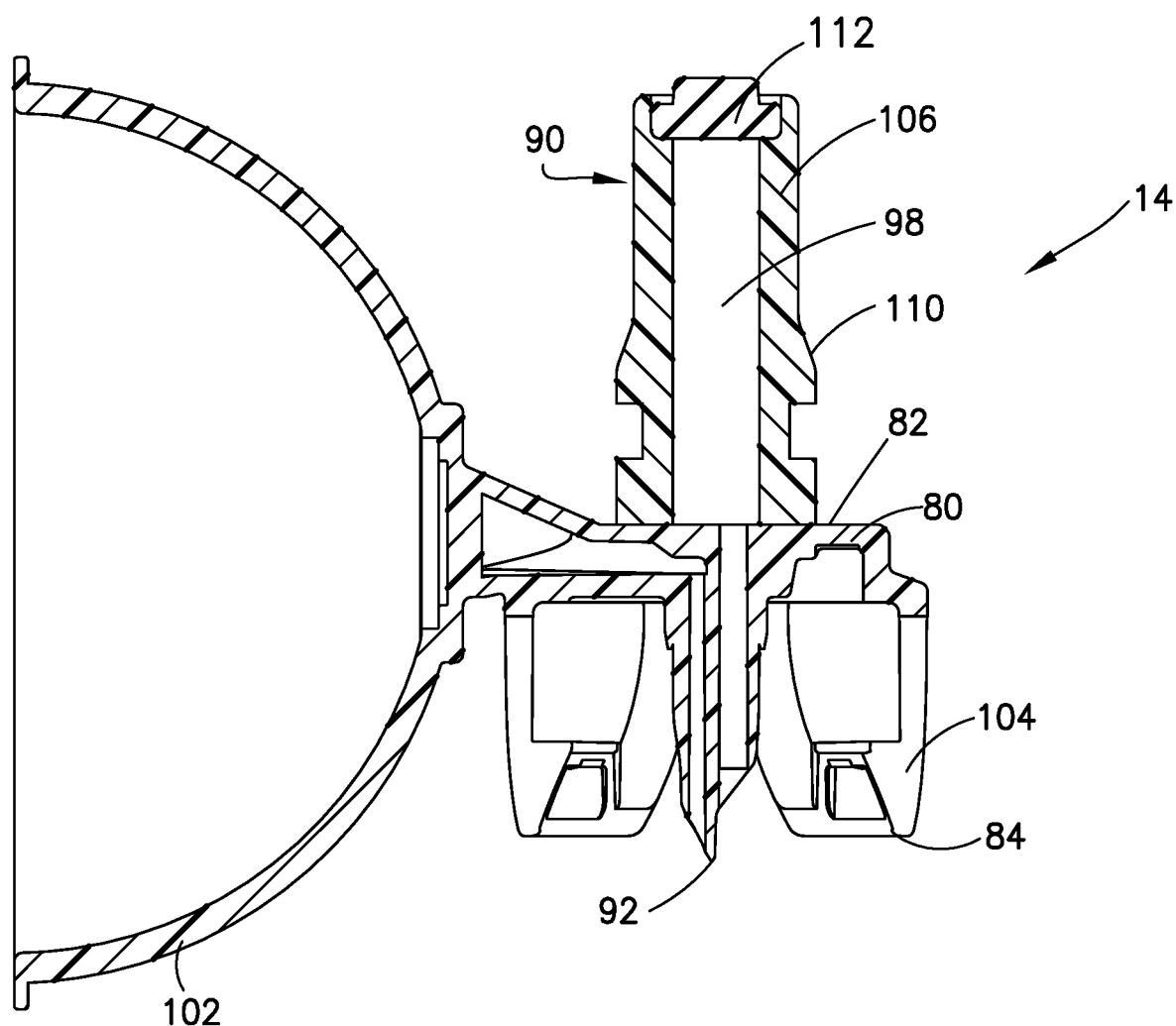
FIG. 19 is a cross-sectional view of the vial adapter along line 19-19 in FIG. 16 according to one aspect of the present invention.

Referring to FIG. 14, the lock member 52 further includes a lead-in surface 68 that is a concave-shaped depression on the bottom of the lock member 52. As discussed below, the lead-in surface 68 is configured to engage a corresponding connection interface to transition the lock member 52 from the closed position to the open position.

Referring to FIGS. 15-19, the vial adapter 14 includes a body 80 having a first end 82 and a second end 84. The first end 82 includes a second connection interface 90 that is configured to mate with and lock with the first connection interface 50 of the syringe adapter 12. The second end 84 includes a spike member 92 that is configured to pierce the vial or container 18. The spike member 92 defines a fluid channel 94 and a vent channel 96. The fluid channel 94 is in fluid communication with a passageway 98 extending through the second connection interface 90. The vent channel 96 is in fluid communication with a pressure equalization device 102, such as a balloon-type or bellows-type pressure equalization arrangement, although any suitable pressure equalization arrangement 102 may be utilized. The pressure equalization arrangement 102 is configured to maintain the pressure within the vial 18 during fluid transfer to prevent the vial 18 from being pressurized or place in a vacuum. The second end 84 of the vial adapter 14 also includes a vial attachment 104 to secure the vial adapter 14 to the vial 18 or other container.

Referring still to FIGS. 15-19, the second connection interface 90 includes a generally cylinder-shaped body 106 that defines a locking surface 108. The second connection interface 90 further includes a lead-in surface 110. The lead-in surface 110 of the second connection interface 90 projects radially outward from the body 106 of the second connection interface 90 and defines a rounded transition between the body 106 and the lead-in surface 110. The lead-in surface 110 is positioned intermediate the ends of the second connection interface 90, although any other suitable position may be utilized. The locking surface 108 is a ring-shaped recess that is recessed relative to the lead-in surface 110 and configured to receive the lock member 52 of the first connection interface 50. The locking surface 108 is defined by 90 degree angles, although other suitable shapes and angles may be utilized. The second connection interface 90 receives a membrane 112 that closes the passageway 98 of the second connection interface 90. The second connection interface 90 is configured to be received within the interior space 28 of the syringe adapter 12 when the lock member 52 of the first connection interface 50 is in the open position and restricted from moving within the interior space 28 of the syringe adapter 12 when the lock member 52 is in the closed position. The lead-in surface 110 of the second connection interface 90 is configured to engage the lock member 52 of the first connection interface 50 to further move the lock member 52 and further bias the cantilever spring 60. When the second connection interface 90 is fully mated to the first connection interface 50, the lock member 52 of the first connection interface 50 is configured to be in the closed position and received within the locking surface 108 to lock the first connection interface 50 from longitudinal and transverse movement relative to the second connection interface 90, but still allowing rotational movement relative thereto.

Referring to FIGS. 20-21, the patient connector 16 includes a body 120 having a first end 122 and a second end 124 and defining a passageway 126 that extends therethrough. The first end 122 of the patient connector 16 also includes the second connection interface 90 that is that same as the second connection interface of the vial adapter 14. Accordingly, the second connection interface 90 of the patient connector 16 includes the same features of the second connection interface 90 of the vial adapter 14 described above and cooperates with the first connection interface 50 in the same manner. The second end 124 of the patient connector 16 includes an IV line attachment 128, such as a male luer connector, although any other suitable connection arrangements may be utilized.

Figure 22:
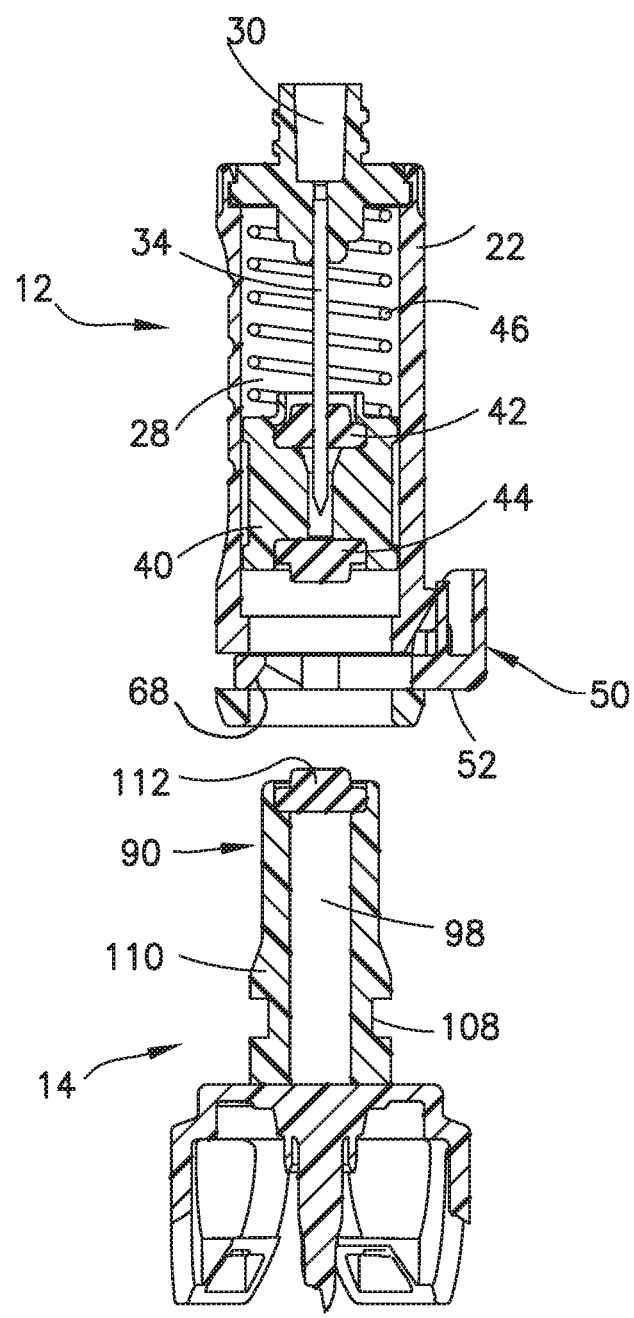
FIG. 22 is a cross-sectional view of the syringe adapter of FIG. 3 prior to being connected to the vial adapter of FIG. 15 according to one aspect of the present invention.
Figure 23:
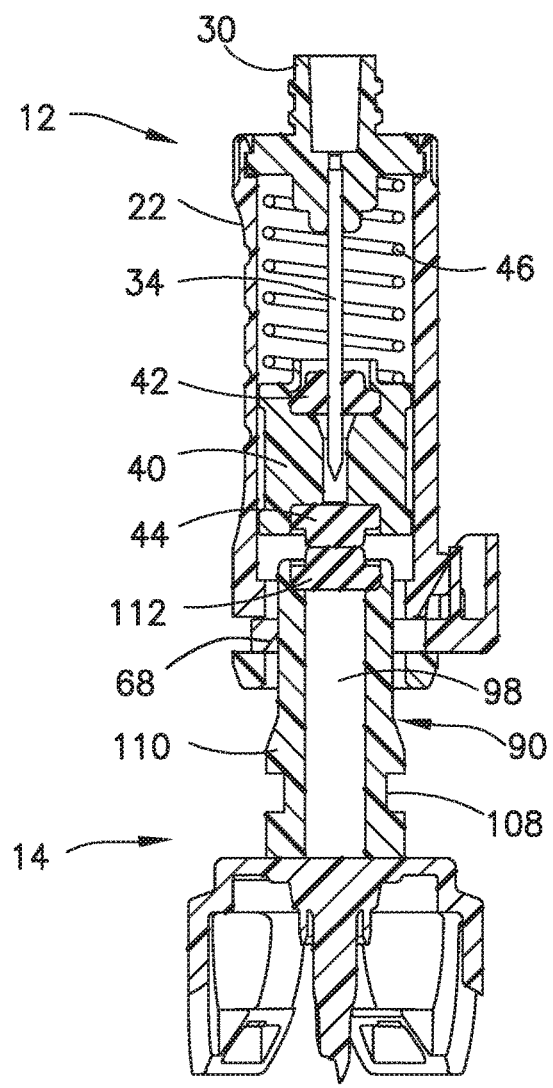
FIG. 23 is a cross-sectional view of the syringe adapter of FIG. 3 in the process of being connected to the vial adapter of FIG. 15 according to one aspect of the present invention.
Figure 24:
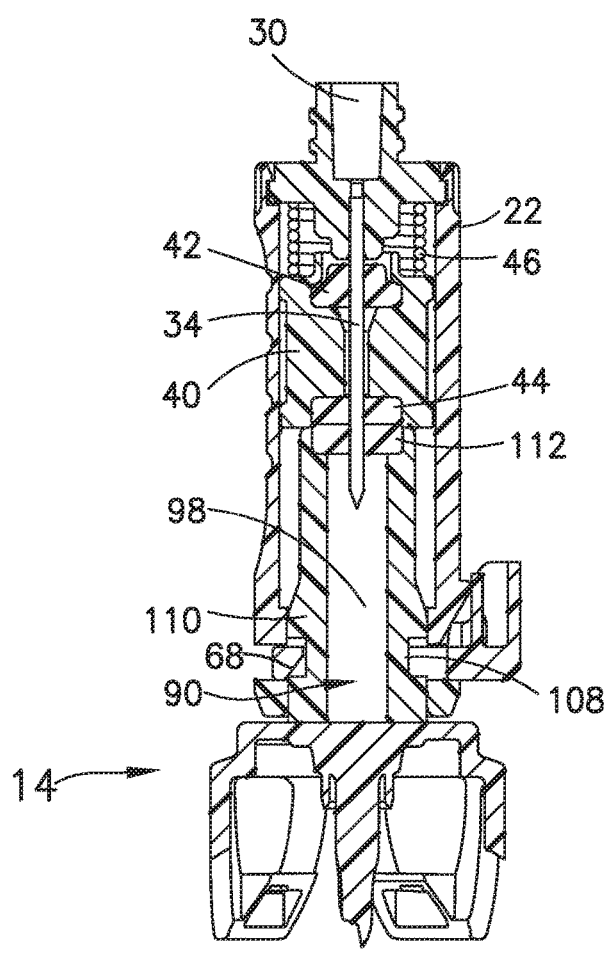
FIG. 24 is a cross-sectional view of the syringe adapter of FIG. 3 connected and locked to the vial adapter of FIG. 15 according to one aspect of the present invention.

Referring to FIGS. 22-24, the process of mating the first connection interface 50 with the second connection interface 90 is shown. Although the syringe adapter 12 with the first connection interface 50 is shown being attached to the vial adapter 14 with the second connection interface 90, the connection of the first connection interface 50 with the second connection interface 90 will be similar regardless of the devices incorporating the first and second connection interfaces 50, 90. As shown in FIG. 22, the interior space 28 of the syringe adapter 12 is aligned with the second connection interface 90 of the vial adapter 14. In particular, the longitudinal axis of the syringe adapter 12 is aligned with the longitudinal axis of the vial adapter 14 and the lock member 52 of the first connection interface 50 is in the closed position. As shown in FIG. 23, the first connection interface 50 and the second connection interface 90 are moved towards each other with a portion of the second connection interface 90 being received within the interior space 28 of the syringe adapter 12. At this position, the lead-in surface 68 of the lock member 52 of the first connection interface 50 engages the second connection interface 90, which transitions the lock member 52 from the closed position (shown in FIG. 22) to the open position (shown in FIG. 23). When the lock member 52 is moved from the closed position to the open position, the cantilever spring 60 will engage the cam surface 62 of the body 22 of the syringe adapter 12, which creates a biasing force that urges the lock member 52 back to the closed position. Such movement back to the closed position, however, is prevented by engagement of the lock member 52 with the body 106 of the second connection interface 90. With the lock member 52 of the first connection interface 50 in the open position, the second connection interface 90 is allowed to continue its movement within the interior space 28 of the syringe adapter 12 to continue the process of mating the syringe adapter 12 to the vial adapter 14 and to move the first connection interface 50 and the second connection interface 90 towards a locked engagement.

Referring to FIGS. 23-24, after the lock member 52 of the first connection interface 50 is moved to the open position, the membrane 112 of the second connection interface 90 engages the second membrane 44 of the seal arrangement 38 of the syringe adapter 12 thereby forming a liquid tight seal during fluid transfer between the syringe adapter 12 and the vial adapter 14. Further insertion of the second connection interface 90 within the interior space 28 of the syringe adapter 12 moves the membrane carrier 40 toward the first end 24 of the syringe adapter 12 against the biasing force of the biasing member 46 and causes cannula 34 to pierce the second membrane 44 of the seal arrangement 38 of the syringe adapter 12 and the membrane 112 of the second connection interface 90 thereby placing the vial adapter 14 in fluid communication with the syringe adapter 12. When the second connection interface 90 is inserted a predetermined distance within the interior space 28 of the syringe adapter 12, the lead-in surface 110 of the second connection interface 90 engages the lock member 52 to further compress the cantilever spring 60. With further movement, the locking surface 108 of the second connection interface 90 will be aligned with the lock member 52 of the first connection interface 50 such that the lock member 52 is received within the locking surface 108. In particular, the lock member 52 is biased towards the closed positioned by the cantilever spring 60 and when the lock member 52 reaches the locking surface 108, the lock member 52 is free to move into the closed position where a portion of the lock member 52 is positioned within the interior space 28 of the syringe adapter 12.

In the position shown in FIG. 24, the first connection interface 50 is fully mated and locked with respect to the second connection interface 90. In such a position, the syringe adapter 12 is prevented from being disconnected from the vial adapter 14 due to the engagement between the lock member 52 of the first connection interface 50 and the locking surface 108 of the second connection interface 90. Although the locked engagement between the first connection interface 50 and the second connection interface 90 prevents axial and transverse movement relative to each other, the first connection interface 50 and the second connection interface 90 are free to rotate relative to each when locked to each other, which advantageously prevents IV line tangling and/or other accidental disengagement or device failure associated with lack of rotation between components. In particular, the patient connector 16, which is mated with and locked to the syringe adapter 12 in the same manner as described above in connection with the vial adapter 14, is typically attached to a patient IV line and the rotation of the first connection interface 50 relative to the second connection interface 90 assists in prevent twisting of a patient IV line connected to the patient connector 16. However, the first connection interface 50 and the second connection interface 90 may be provided with a keyed surface arrangement to prevent such relative rotation if desired.

Referring again to FIGS. 22-24, in order to disconnect the first connection interface 50 from the second connection interface 90, the button 58 of the lock member 52 of the first connection interface 50 is engaged by a user and pushed radially inward to transition the lock member 52 from the closed position to the open position. The second connection interface 90 can then be removed from the interior space 28 of the syringe adapter 12 in the reverse order of the steps to connect the first connection interface 50 to the second connection interface 90. When the second connection interface 90 is finally separated from the first connection interface 50, the lock member 52 is moved to the closed position and the biasing member 46 of the seal arrangement 38 of the syringe adapter 12 moves the membrane carrier 40 to its original position with the distal end 36 of the cannula 34 positioned between the first and second membranes 42, 44. Although the first and second connection interfaces 50, 90 are each provided with the lead-in surfaces 68, 110, only one of the first and second connection interfaces 50, 90 may be provided with a lead-in surface 68, 110. Furthermore, neither of the first and second connection interfaces 50, 90 may be provided with the lead-in surfaces 68, 110, which will require the lock member 52 of the first connection interface 50 to be manually moved from the closed position to the open position to allow mating of the first and second connection interfaces 50, 90. More specifically, the lock member 52 of the first connection interface 50 may be moved from the closed position to the open position by engaging the button 58 of the lock member 52 and moving the lock member 52 radially inward such that the lock member 52 is moved to the open position thereby allowing the mating of the first and second connection interfaces 50, 90.

Figure 25:
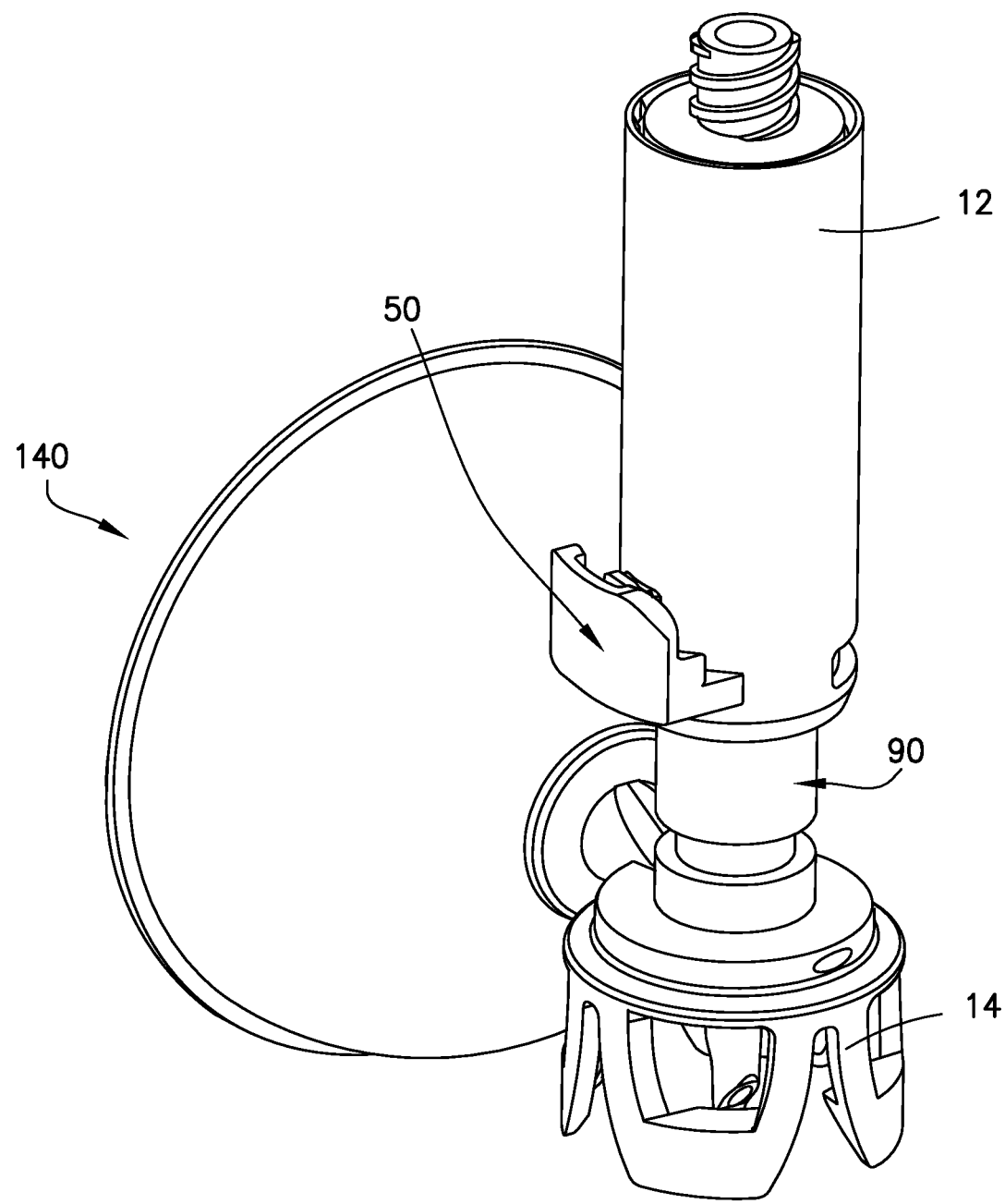
FIG. 25 is a perspective view of a system according to a second aspect of the present invention.
Figure 26:
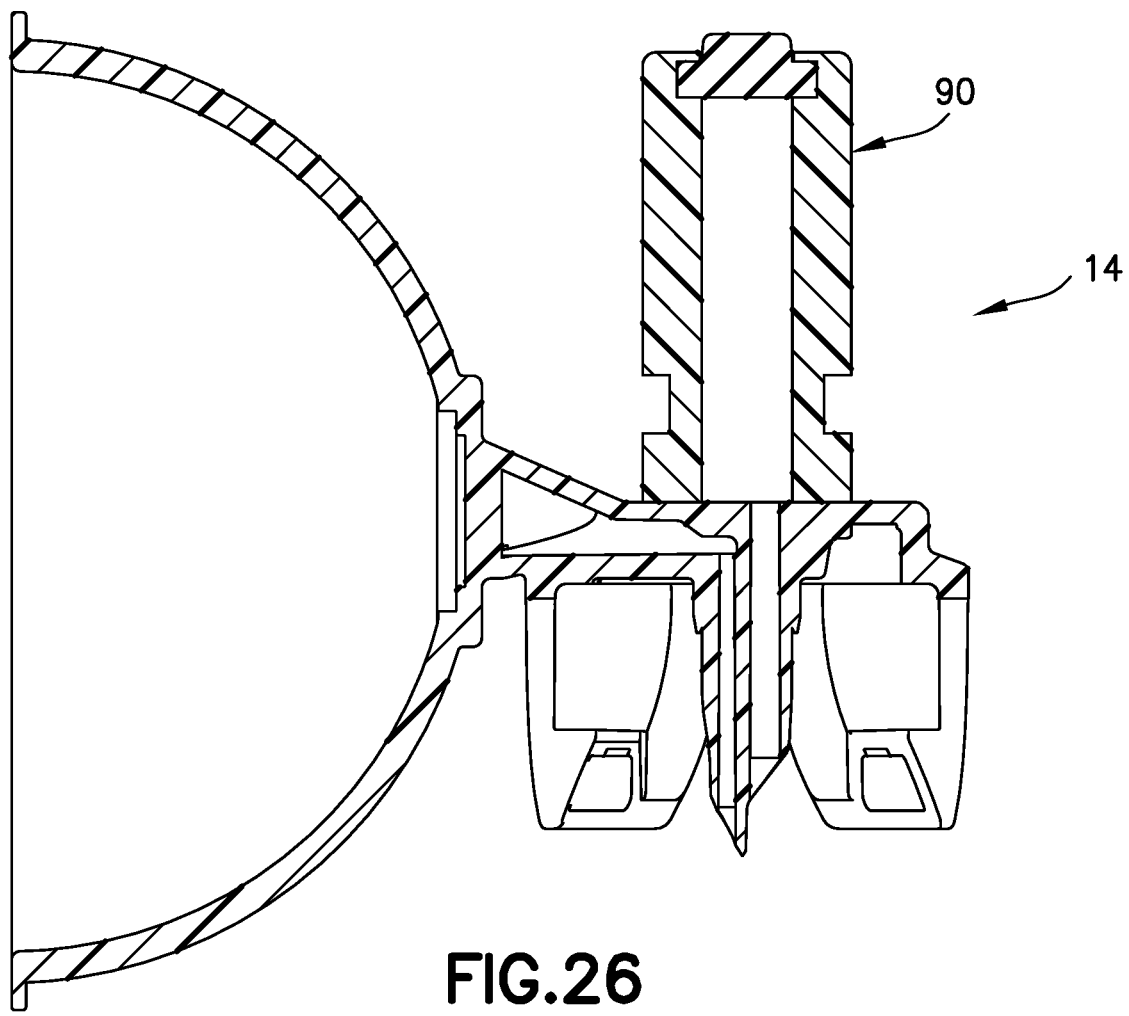
FIG. 26 is a cross-sectional view of a vial adapter of the system of FIG. 25 according to one aspect of the present invention.

Referring to FIGS. 25-27, a second aspect of a system 140 for the closed transfer of fluids is provided. The system 140 is similar to the system 10 shown in FIGS. 1 and 2 with like reference numbers used for like elements. Rather than providing a lead-in surface that extends radially outward and positioned intermediate the ends of the body of the second connection interface 90, the second connection interface 90 of the system 140 shown in FIGS. 25-27 includes a lead-in surface at the first end of the second connection interface 90 adjacent the membrane. The lead-in surface of the aspect shown in FIGS. 25-27 is embodied as a slight blend at the top of the connection interface 90 and assists in moving the lock member 52 from the closed to the open position. Further, the body 22 of the syringe adapter 12 does not include any grip structures.

Although not shown, the systems shown in FIGS. 1-27, may include one or more indication arrangements to provide a user with feedback when the connection interfaces are fully locked or separated. In particular, the body 22 of the syringe adapter 12 may be provided with openings with inner and outer tubes that cover one another when the part is in the locked position and not cover one another when the part is in the initial or unlocked position. Alternatively, only one color change component may be provided that is visible within the opening in the body of the syringe adapter 12 when the device is in the locked or unlocked position. The first and second connection interfaces 50, 90 may also be provided with one or more tactile or auditory indicators to provide an indication of the state of the connection between the first and second connection interfaces 50, 90. The indication arrangement may also be embodied as alignment lines, dots, symbols, words, or other suitable indicia to assist a user in operating the system. Furthermore, although the seal arrangement 38 of the syringe adapter 12 includes a membrane carrier 40 and first and second membranes 42, 44, any other suitable arrangement for sealing and delivering a fluid may be provided.

Referring to FIG. 28, the position of the cantilever spring 60 of the lock member 52 and the cam surface 62 of the body 22 of the syringe adapter 12 may be reversed. For example, as shown in FIG. 28, the body 22 of the syringe adapter 12 is formed with a biasing member 144, such as a cantilever spring, that is configured to contact a cam surface 146 provided on the lock member 52 of the first connection interface 50. The lock member 52 operates in the same manner as described above in connection with system 10.

Figure 29:
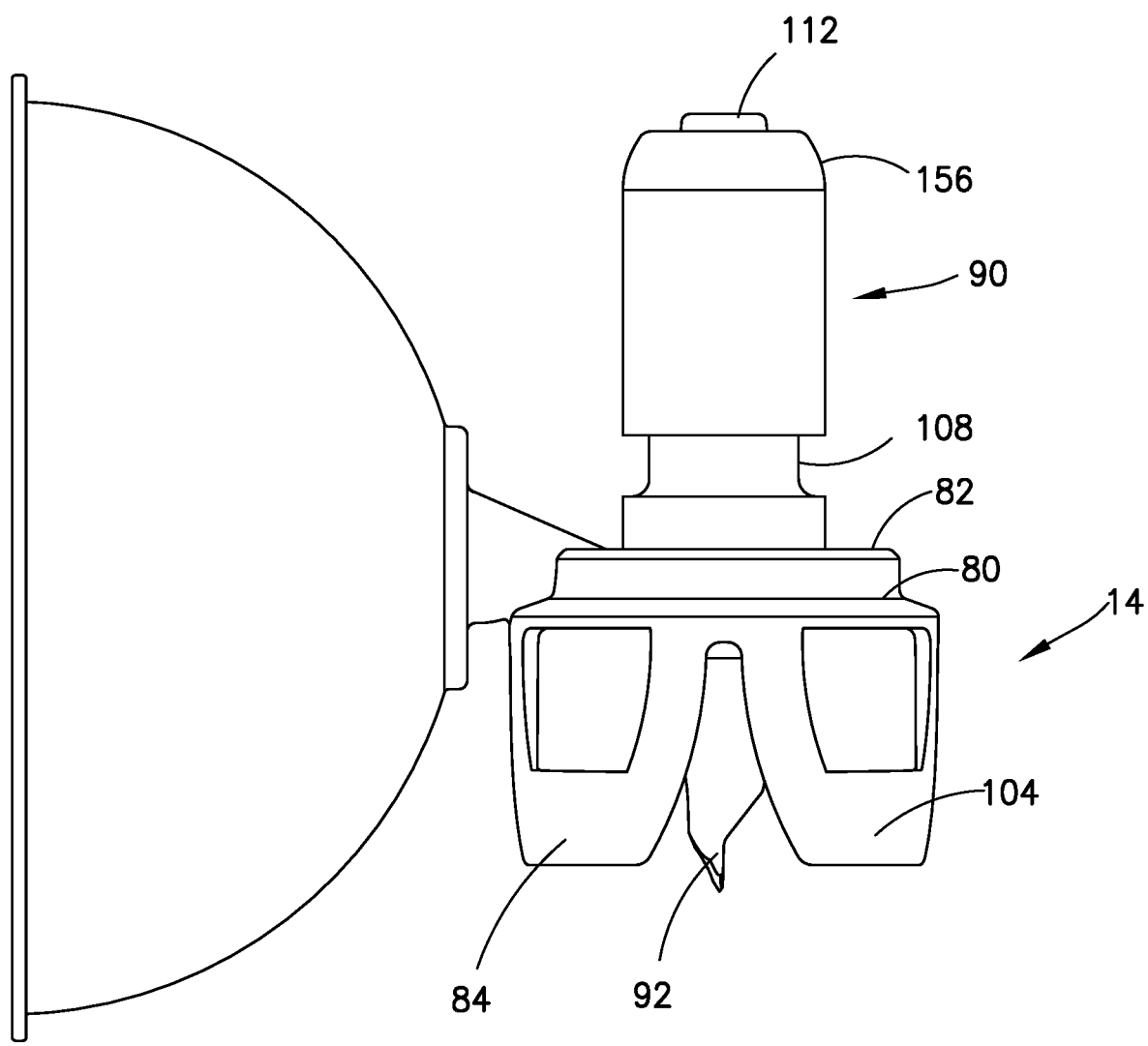
FIG. 29 is a front view of a vial adapter according to yet another aspect of the present invention.

Referring to FIG. 29, a further aspect of the second connection interface 90 is shown. The second connection interface 90 shown in FIG. 29 is similar to aspects of the second connection interface shown in FIGS. 1-28 and described above. The second connection interface 90 of FIG. 29, however, includes a lead-in surface 156 positioned adjacent to the membrane 112 or first end of the second connection interface 90. The lead-in surface 156 assists in moving the lock member 52 from the closed to the open position. The second connection interface 90 shown in FIG. 29 is provided in connection with a vial adapter, although this aspect may be utilized in connection with any medical device and any component of a system for the closed transfer of fluids.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe adapter comprising:
   a body having a proximal end and a distal end, the body defining an interior space, the proximal end of the body configured to be connected to a first container, the distal end of the body including a lock member having an open position where the lock member is configured to receive a connection interface and a closed position where the lock member is configured to be engaged with the connection interface, the lock member including at least one radially extending projection configured to engage a corresponding projection of the body to retain the lock member to the body;
   a seal arrangement positioned within the body, the seal arrangement comprising:
      a membrane carrier configured to move within the body;
      a membrane received by the membrane carrier; and
      a biasing member engaging the membrane carrier such that a distal end of the membrane is positioned distally of a position at which the biasing member engages the membrane carrier; and
   a cannula positioned within the body and extending at least partially through the membrane,
   wherein the proximal end of the body defines a plurality of recessed portions each extending in a longitudinal direction adjacent to an end face of the body, the plurality of recessed portions spaced around a circumference of the body to enhance gripping of the syringe adapter,
   wherein the body defines a plurality of annular grooves that extend around the circumference of the body,
   wherein the lock member comprises a pair of axially extending projections positioned adjacent a button that is configured to be engaged by a hand of a user of the syringe adapter to move the lock member from the closed position to the open position, and wherein the pair of axially extending projections are configured to engage an external surface of the syringe adapter when the lock member is in the open position.

2. The syringe adapter of claim 1, wherein the membrane carrier is biased toward the second end of the body via the biasing member.

3. The syringe adapter of claim 1, wherein the body defines an opening extending transversely relative to a longitudinal axis of the body that receives the lock member, the lock member configured to move relative to the body between the open position and the closed position.

4. The syringe adapter of claim 3, wherein the lock member comprises a biasing member that is configured to bias the lock member towards the closed position.

5. The syringe adapter of claim 4, wherein the lock member comprises a lead-in surface that is configured to contact the connection interface and move the lock member from the closed position to the open position when the syringe adapter is mated with the connection interface.

6. The syringe adapter of claim 4, wherein the biasing member of the lock member comprises a cantilever spring, the body defining a cam surface configured to engage the cantilever spring of the lock member.

7. The syringe adapter of claim 6, wherein the cantilever spring extends in an axial direction, and wherein the cam surface extends radially outward from the body.

8. The syringe adapter of claim 1, wherein the at least one radially extending projection of the lock member comprises a pair of radially extending projections positioned on opposite sides of the lock member, and wherein the at least one corresponding projection of the body comprises a pair of corresponding projections configured to engage the pair of projections of the lock member.

9. The syringe adapter of claim 8, wherein the lock member is annular and received within an opening defined by the body, the opening of the body extending transversely relative to a longitudinal axis of the body.

10. The syringe adapter of claim 1, wherein the lock member comprises a button that is configured to be engaged by a hand of a user to move the lock member from the closed position to the open position.

11. The syringe adapter of claim 1, wherein the first end of the body includes a female luer connector configured to be secured to a syringe.

12. The syringe adapter of claim 1, wherein the pair of axially extending projections further comprise a curved portion to engage an external surface of the syringe adapter for preventing lateral movement of the lock member when the lock member is in the open position.

* * * * *